US010185012B2

(12) United States Patent
Ye et al.

(10) Patent No.: US 10,185,012 B2
(45) Date of Patent: Jan. 22, 2019

(54) SYSTEM AND METHOD FOR MAGNETIC RESONANCE IMAGING

(71) Applicant: SHANGHAI UNITED IMAGING HEALTHCARE CO., LTD., Shanghai (CN)

(72) Inventors: Yongquan Ye, Houston, TX (US); Jinguang Zong, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 90 days.

(21) Appl. No.: 15/314,059

(22) PCT Filed: Jul. 14, 2016

(86) PCT No.: PCT/CN2016/089986
§ 371 (c)(1),
(2) Date: Nov. 25, 2016

(87) PCT Pub. No.: WO2018/010134
PCT Pub. Date: Jan. 18, 2018

(65) Prior Publication Data
US 2018/0231631 A1    Aug. 16, 2018

(51) Int. Cl.
*G01V 3/00*  (2006.01)
*G01R 33/56*  (2006.01)
(Continued)

(52) U.S. Cl.
CPC .......... *G01R 33/5608* (2013.01); *A61B 5/055* (2013.01); *G01R 33/24* (2013.01);
(Continued)

(58) Field of Classification Search
CPC .................................................. G01R 33/5608
(Continued)

(56) References Cited

U.S. PATENT DOCUMENTS 6,658,280 B1  12/2003  Haacke
7,657,074 B2   2/2010  Haras
(Continued)

FOREIGN PATENT DOCUMENTS

CN     101352339 A   1/2009
CN     103513202 A   1/2014
(Continued)

OTHER PUBLICATIONS

International Search Report for PCT/CN2016/089986 dated Mar. 1, 2017, 4 pages.
(Continued)

*Primary Examiner* — Louis Arana
(74) *Attorney, Agent, or Firm* — Metis IP LLC

(57) ABSTRACT

A system and method for magnetic resonance imaging is provided. The method includes acquiring a plurality of echo signals relating to a region of interest of a subject at a number of echo times; generating a plurality of phase images based on the plurality of echo signals; generating an unwrapped phase map by performing a phase unwrapping correction to the plurality of phase images; generating a virtual phase map based on the unwrapped phase map; determining a phase mask based on the virtual phase map; obtaining magnitude information of the plurality of echo signals; and generating a susceptibility weighted image based on the phase mask and the magnitude information.

20 Claims, 14 Drawing Sheets

(51) Int. Cl.
G01R 33/565 (2006.01)
G01R 33/24 (2006.01)
G01R 33/561 (2006.01)
A61B 5/055 (2006.01)
G01R 33/60 (2006.01)
G06T 11/00 (2006.01)
G01R 33/48 (2006.01)
G01R 33/50 (2006.01)
G01R 33/563 (2006.01)

(52) U.S. Cl.
CPC ......... *G01R 33/56* (2013.01); *G01R 33/5602* (2013.01); *G01R 33/5613* (2013.01); *G01R 33/5615* (2013.01); *G01R 33/56545* (2013.01); *G01R 33/60* (2013.01); *G01R 33/481* (2013.01); *G01R 33/4824* (2013.01); *G01R 33/50* (2013.01); *G01R 33/5616* (2013.01); *G01R 33/5635* (2013.01); *G06T 11/003* (2013.01)

(58) Field of Classification Search
USPC .................................................. 324/307, 309
See application file for complete search history.

(56) References Cited

U.S. PATENT DOCUMENTS

| 9,097,782 | B2 | 8/2015 | Haacke | |
| 9,165,386 | B2* | 10/2015 | Sato ...................... | A61B 5/055 |
| 2003/0212322 | A1 | 11/2003 | Haacke | |
| 2004/0010191 | A1 | 1/2004 | Yatsui | |
| 2008/0055308 | A1 | 3/2008 | Dekel et al. | |
| 2009/0261824 | A1* | 10/2009 | Haacke ............. | G01R 33/56536 |
| | | | | 324/307 |
| 2013/0002247 | A1 | 1/2013 | Haacke et al. | |
| 2013/0202181 | A1 | 8/2013 | Lo et al. | |
| 2014/0210467 | A1 | 7/2014 | Hwang et al. | |
| 2015/0078644 | A1 | 3/2015 | Park et al. | |
| 2015/0362575 | A1 | 12/2015 | Ourselin et al. | |
| 2017/0059682 | A1* | 3/2017 | Dagher ................ | G01R 33/243 |
| 2018/0017652 | A1* | 1/2018 | Ye ...................... | G01R 33/5602 |

FOREIGN PATENT DOCUMENTS

| EP | 2015171949 A1 | 11/2015 |
| WO | 2002013693 A1 | 2/2002 |

OTHER PUBLICATIONS

Written Opinion for PCT/CN2016/089986 dated Mar. 1, 2017, 4 pages.
E. Mark Haacke et al, "Susceptibility weighted imaging (SWI)." Magnetic Resonance in Medicine 52: 612-618 (2004).
Andreas Deistung et al . "ToF-SWI: simultaneous time of flight and fully flow compensated susceptibility weighted imaging." Journal of Magnetic Resonance Imaging 29: 1478-1484 (2009).
Yongquan Ye et al. "Noncontrast-enhanced magnetic resonance angiography and venography imaging with enhanced angiography." Journal of Magnetic Resonance Imaging 38: 1539-1548 (2013).
Wei Feng et al. "Catalytic multiecho phase unwrapping scheme (CAMPUS) in multiecho gradient echo imaging: removing phase wraps on a voxel-by-voxel basis." Magnetic Resonance in Medicine 70: 117-126 (2013).
Simon Robinson et al. "Combining phase images from multi-channel RF coils using 3D phase offset maps derived from a dual-echo scan." Magnetic Resonance in Medicine 65: 1638-1648 (2011).
E. Mark Haacke et al. "Quantitative susceptibility mapping: current status and future directions." Magnetic Resonance in Medicine 33(1): 1-25 (2014).
Yi Wang et al. "Quantitive susceptability mapping (QSM): Decoding MRI data for a tissue magnetic biomarker." Magnetic Resonance in Medicine 73: 82-101 (2015).
Bing Wu et al. "Quantitative susceptibility mapping (QSM): Decoding MRI data for a tissue magnetic biomarker." Magnetic Resonance in Medicine 73: 82-101 (2015).
Tian Liu et al. "A novel background field removal method for MRI using projection onto dipole fields (PDF)," NMR in Biomedicine 24(9): 1129-1136 (2011).
Hussein S. Abdul-Rahman et al. "Fast and robust three-dimensional best path phase unwrapping algorithm."Appiied Optics. 46(26): 6623-6634 (2007).
Kathryn E. Hammond et al. "Development of a robust method for generating 7T multichannel phase images of the brain with application to normal volunteers and patients with neurological diseases." Neuroimage 39(4): 1682-1692 (2008).
Robert W. Brown et al. "Magnetic Resonance Imaging: Physical Principles and Sequence Design." 2nd edition. New York: Wiley-Liss: 669-693 (2014).
Ferdinand Schweser et al. "Quantitative imaging of intrinsic magnetic tissue properties using MRI signal phase: An approach to in vivo brain iron metabolism?" NeuroImage 54(4): 2789-2807 (2011).

* cited by examiner

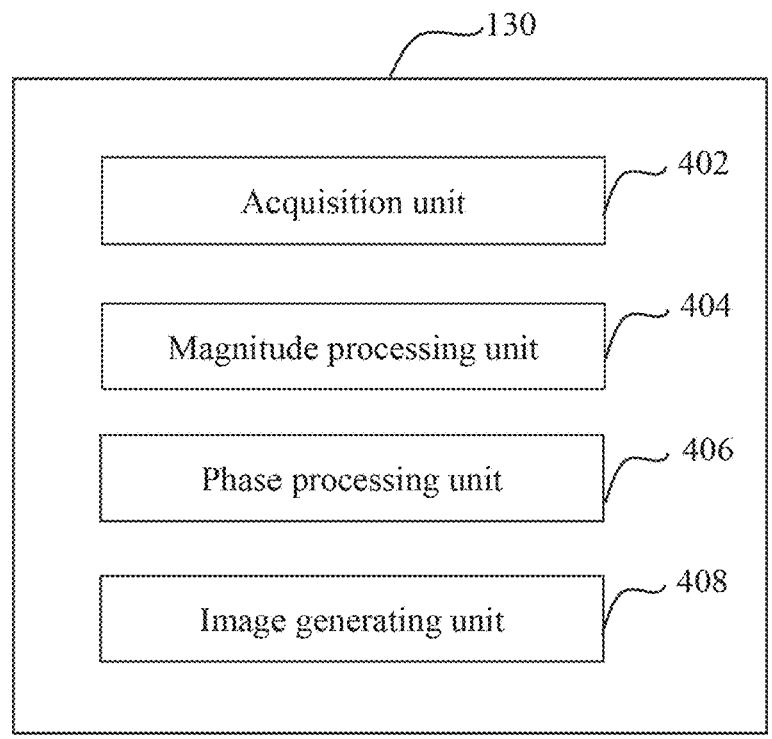
FIG. 4-A
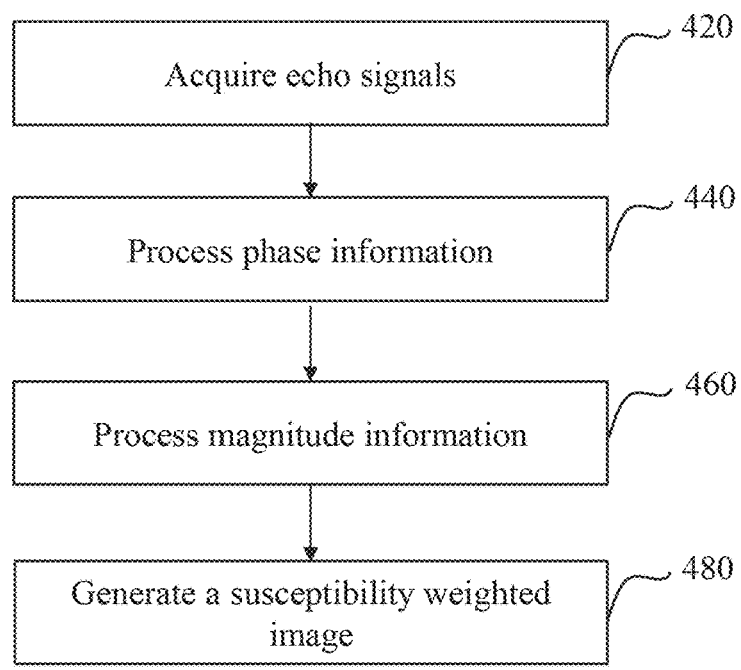
FIG. 4-B

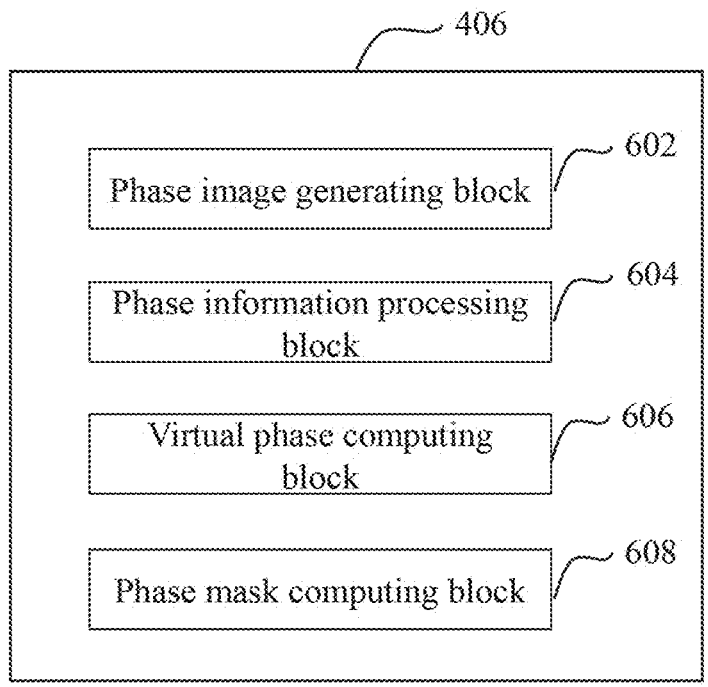
FIG. 6-A
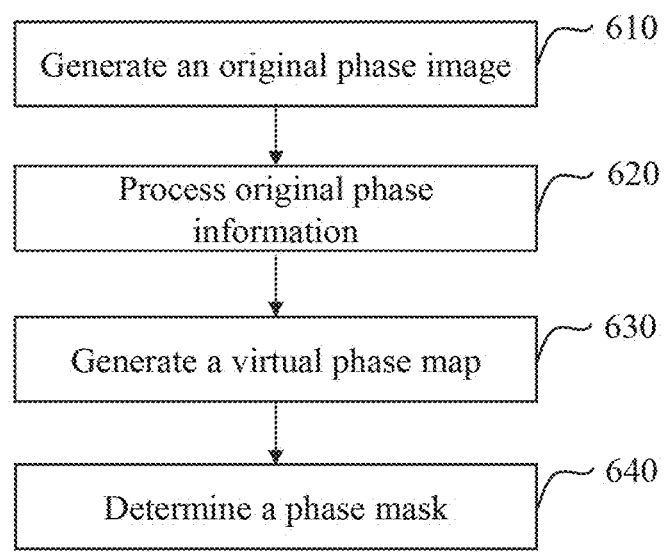
FIG. 6-B

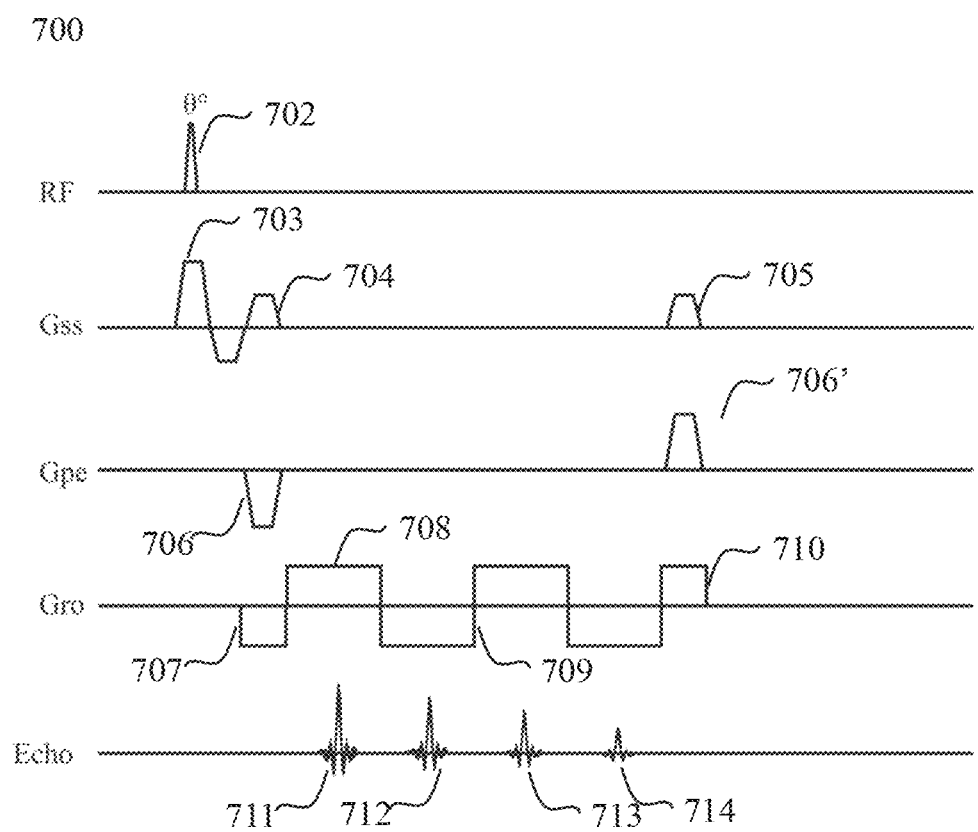
FIG. 7-A

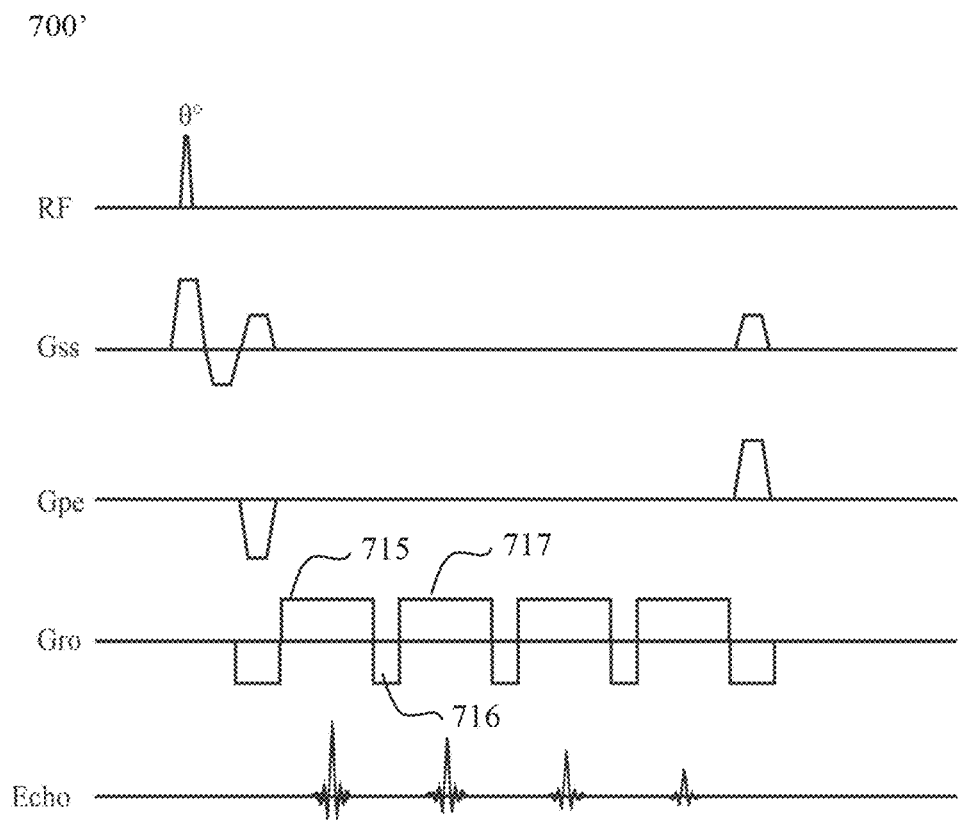
FIG. 7-B

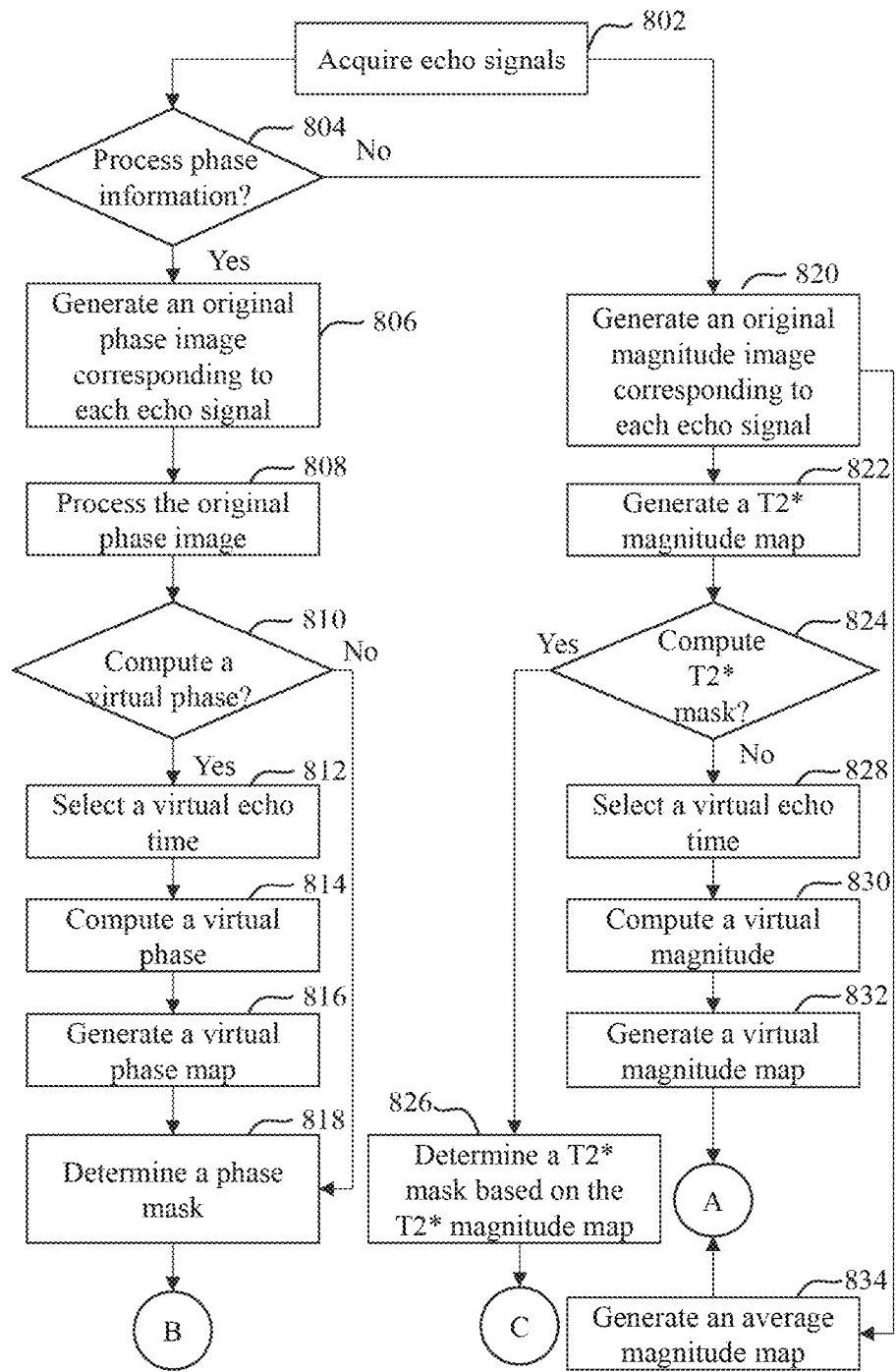
FIG. 8-A

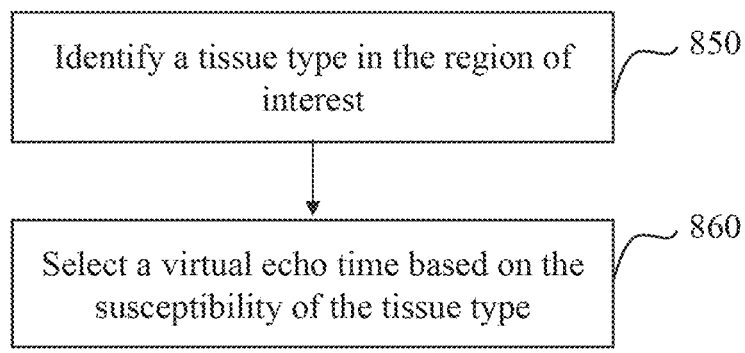
FIG. 8-B
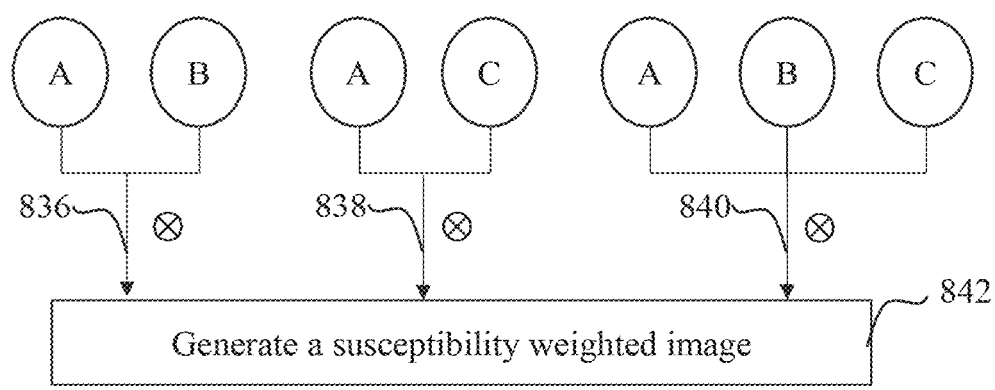
FIG. 8-C

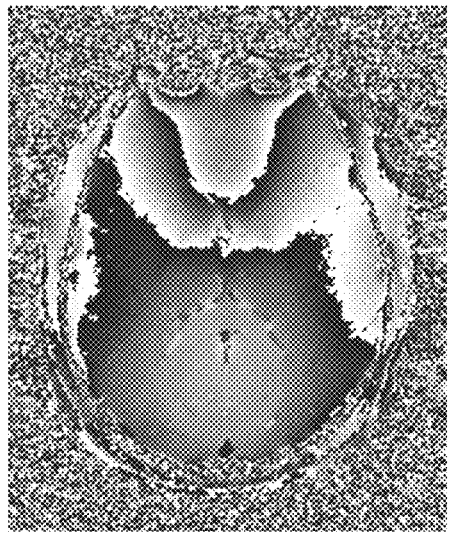
FIG. 9-A
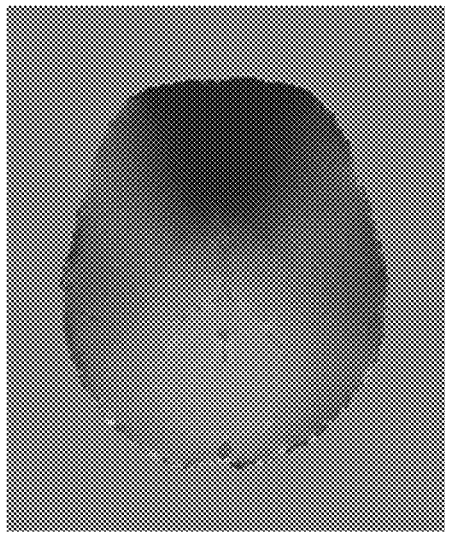
FIG. 9-B
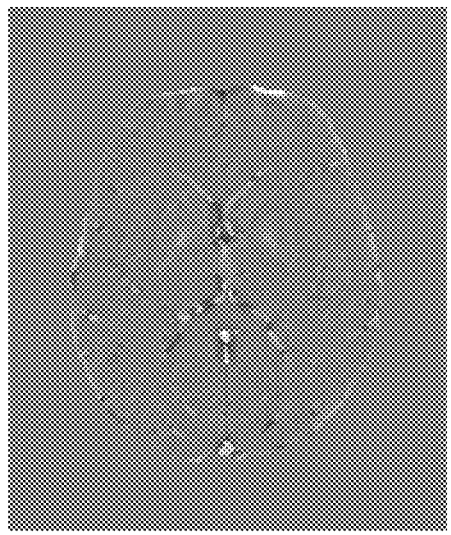
FIG. 9-C

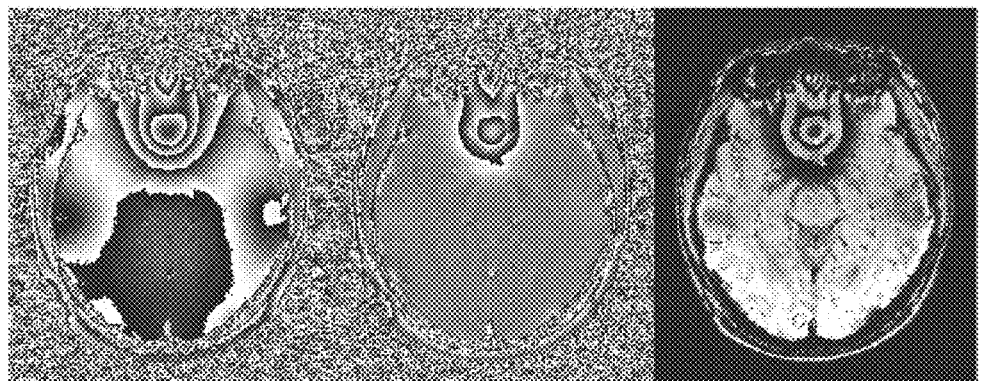
FIG. 10-A    FIG. 10-B    FIG. 10-C
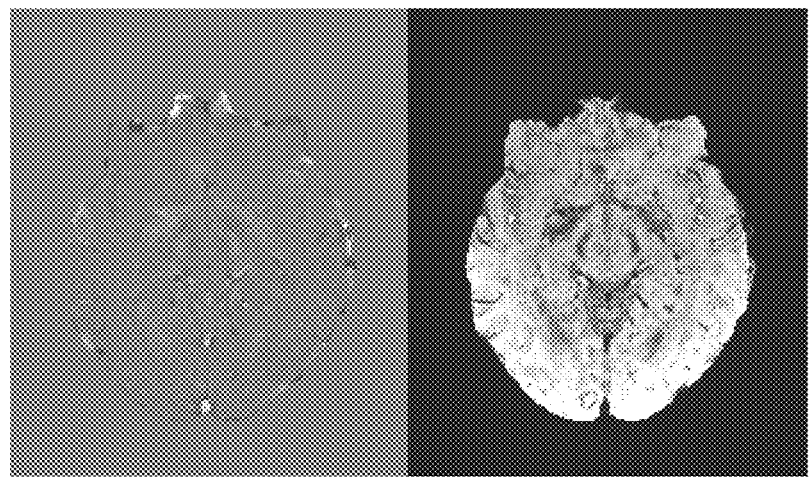
FIG. 10-D    FIG. 10-E

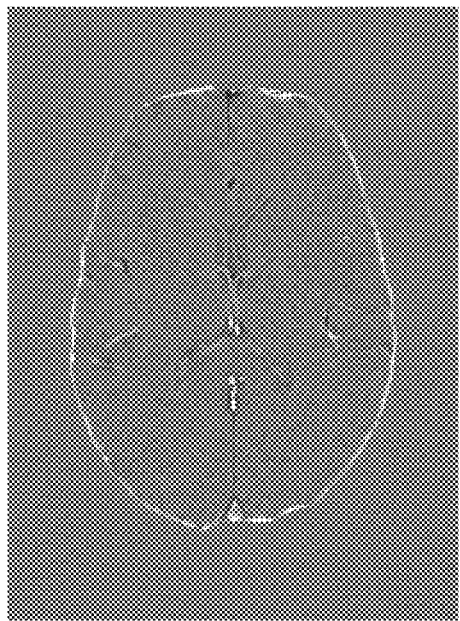
FIG. 11-A
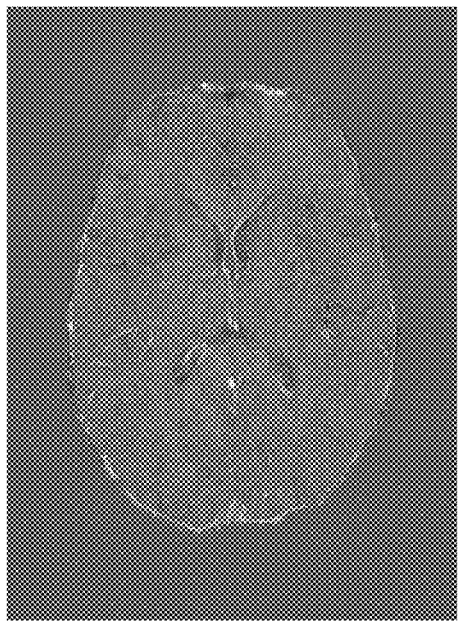
FIG. 11-B
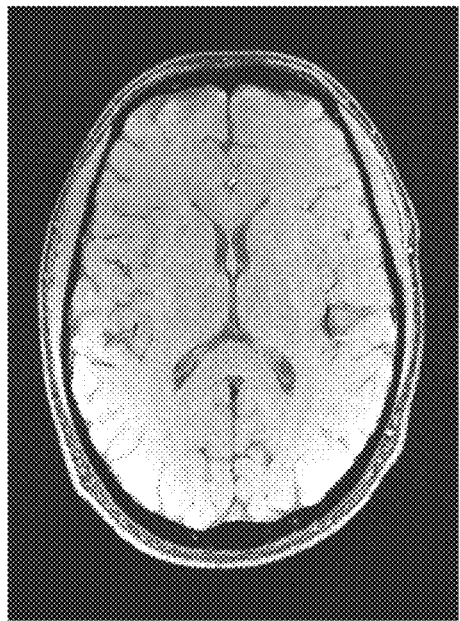
FIG. 11-C

FIG. 12-A  FIG. 12-B  FIG. 12-C under 35 U.S.C. § 371 of International Application No. PCT/CN2016/089986, filed on Jul. 14, 2016, designating the United States of America, the contents of which are incorporated herein by reference.

SYSTEM AND METHOD FOR MAGNETIC RESONANCE IMAGING

CROSS-REFERENCE TO RELATED APPLICATIONS

This present application is a U.S. national stage under 35 U.S.C. § 371 of International Application No. PCT/CN2016/089986, filed on Jul. 14, 2016, designating the United States of America, the contents of which are incorporated herein by reference.

TECHNICAL FIELD

The present disclosure generally relates to magnetic resonance imaging (MRI), and more particularly, to a system and method for susceptibility weighted imaging (SWI) in MRI.

BACKGROUND

Susceptibility weighted imaging (SWI) is an imaging method that may enhance the contrasts of different tissues presented in an image by combining phase information and magnitude information. In traditional susceptibility weighted imaging, a single gradient echo sequence is used and only a single-echo signal is acquired with a long echo time (TE). However, for some tissues with strong susceptibility (e.g., hemorrhage or cavities), wrapped phase of high spatial frequency may be generated, which may lead to image artifacts and a saturated imaging contrast. Therefore, it is desirable to provide a system and method to improve the imaging contrast of different tissues with different susceptibilities.

SUMMARY

In a first aspect of the present disclosure, a method for generating a magnetic resonance (MR) image is provided. The method may include one or more of the following operations. A plurality of echo signals relating to a region of interest of a subject at a number of echo times may be acquired. Each echo signal may correspond to an echo time. A plurality of phase images based on the plurality of echo signals may be generated. Each phase image may correspond to an echo signal. An unwrapped phase map may be generated by performing a phase unwrapping correction to the plurality of phase images. A virtual phase map may be generated based on the unwrapped phase map. The virtual phase map may include at least a virtual phase corresponding to a virtual echo time. A phase mask may be determined based on the virtual phase map. Magnitude information of the plurality of echo signals may be obtained. A susceptibility weighted image may be generated based on the phase mask and the magnitude information.

In some embodiments, the virtual echo time may be a positive number.

In some embodiments, a flow compensation may be performed along a readout direction and/or a phase encoding direction during the acquiring the plurality of echo signals.

In some embodiments, the virtual echo time may relate to a feature of a tissue in the region of interest. The feature of the tissue type may include the susceptibility of the tissue type.

In some embodiments, a field distribution map may be obtained according to phase information of the plurality of phase images. A virtual echo time may be determined based on the field distribution map. A virtual phase may be determined based on the virtual echo time and the field distribution map.

In some embodiments, the virtual phase may be determined using a method selected from linear interpolation, the least square method, or linear regression.

In some embodiments, a background field may be eliminated from the plurality of phase images. In some embodiments, a background field may be eliminated from the virtual phase map.

In some embodiments, a normalization may be applied to the virtual phase map.

In some embodiments, the magnitude information may include an original magnitude image, a virtual magnitude map, an average magnitude map, a T2* magnitude map, or a T2* mask.

In some embodiments, the virtual magnitude map may be generated based on the T2* magnitude map.

In some embodiments, the virtual magnitude map may include a virtual magnitude determined based on the original magnitude image.

In some embodiments, the virtual magnitude may be determined using a method selected from linear interpolation, the least square method, or linear regression.

In some embodiments, a weighted result of the phase mask and the T2* mask may be computed. The susceptibility weighted image may be obtained by multiplying the weighted result by at least one of the original magnitude image, the virtual magnitude map, or the average magnitude map.

In some embodiments, the susceptibility weighted image may be obtained multiplying the phase mask by at least one of the original magnitude image, the virtual magnitude map, or the average magnitude map.

In some embodiments, a minimum intensity projection may be performed on the susceptibility weighted image.

In a second aspect of the present disclosure, a system for generating a magnetic resonance (MR) image is provided. The system may include an acquisition unit, a phase processing unit, a magnitude processing unit and an imaging generating unit. The acquisition unit may be configured to acquire a plurality of echo signals relating to a region of interest of a subject at a number of echo times, each echo signal corresponding to an echo time. The phase processing unit may be configured to process phase information of the echo signals. The magnitude processing unit may be configured to obtain magnitude information of the plurality of echo signals. The imaging generating unit may be configured to generate a susceptibility weighted image based on the phase mask and the magnitude information. The phase processing unit may include a phase image generating block, a phase information processing block, a virtual phase computing block and a phase mask computing block. The phase image generating block may be configured to generate a plurality of phase images based on the plurality of echo signals, each phase image relating to an echo signal. The phase information processing block may be configured to generate an unwrapped phase map by performing a phase unwrapping correction to the plurality of phase images. The virtual phase computing block may be configured to generate a virtual phase map based on the unwrapped phase map. The virtual phase map may include at least a virtual phase corresponding to a virtual echo time. The phase mask computing block may be configured to determine a phase mask based on the virtual phase map.

In some embodiments, the virtual phase computing block may be further configured to obtain a field distribution map according to phase information of the plurality of phase images; determine, based on the field distribution map, a virtual echo time; and determine, based on the virtual echo time and the field distribution map, a virtual phase.

In some embodiments, the virtual echo time may be a positive number.

In some embodiments, the magnitude information may include an original magnitude image, a virtual magnitude map, an average magnitude map, a T2* magnitude map, or a T2* mask.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 4-A is a block diagram illustrating an architecture of a processing module according to some embodiments of the present disclosure;

FIG. 4-B is a flowchart illustrating a process for generating a susceptibility weighted image according to some embodiments of the present disclosure;

FIG. 6-A is a block diagram illustrating an architecture of a phase processing unit according to some embodiments of the present disclosure;

FIG. 6-B is a flowchart illustrating a process for determining a phase mask according to some embodiments of the present disclosure;

FIG. 7-A illustrates an exemplary gradient echo sequence including monopolar readout gradients according to some embodiments of the present disclosure;

FIG. 7-B illustrates an exemplary gradient echo sequence including bipolar readout gradients according to some embodiments of the present disclosure;

FIG. 8-A illustrates an exemplary process for generating a susceptibility weighted image according to some embodiments of the present disclosure;

FIG. 8-B illustrates an exemplary process for selecting a virtual echo time according to some embodiments of the present disclosure;

FIG. 8-C illustrates an exemplary process for generating a susceptibility weighted image according to some embodiments of the present disclosure;

FIG. 9-A through FIG. 9-C provide three exemplary images produced by the signals acquired from a brain MRI with different image processing techniques according to some embodiments of the present disclosure;

FIG. 10-A through FIG. 10-E provide five exemplary images produced by the signals acquired from a brain with different image producing procedures according to some embodiments of the present disclosure;

FIG. 11-A through FIG. 11-C provide three exemplary images or maps produced by the signals acquired from a brain with different image producing procedures according to some embodiments of the present disclosure; and FIG. 12-A through FIG. 12-C provide three exemplary minimum intensity projections produced by the signals acquired from a brain MRI with different image processing techniques according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirits and scope of the present disclosure. Thus, the present disclosure is not limited to the embodiments shown, but to be accorded the widest scope consistent with the claims.

It will be understood that the term "system," "unit," "module," and/or "block" used herein are one method to distinguish different components, elements, parts, section or assembly of different level in ascending order. However, the terms may be displaced by other expression if they may achieve the same purpose.

It will be understood that when a unit, module or block is referred to as being "on," "connected to" or "coupled to" another unit, module, or block, it may be directly on, connected or coupled to the other unit, module, or block, or intervening unit, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

Figure 1:
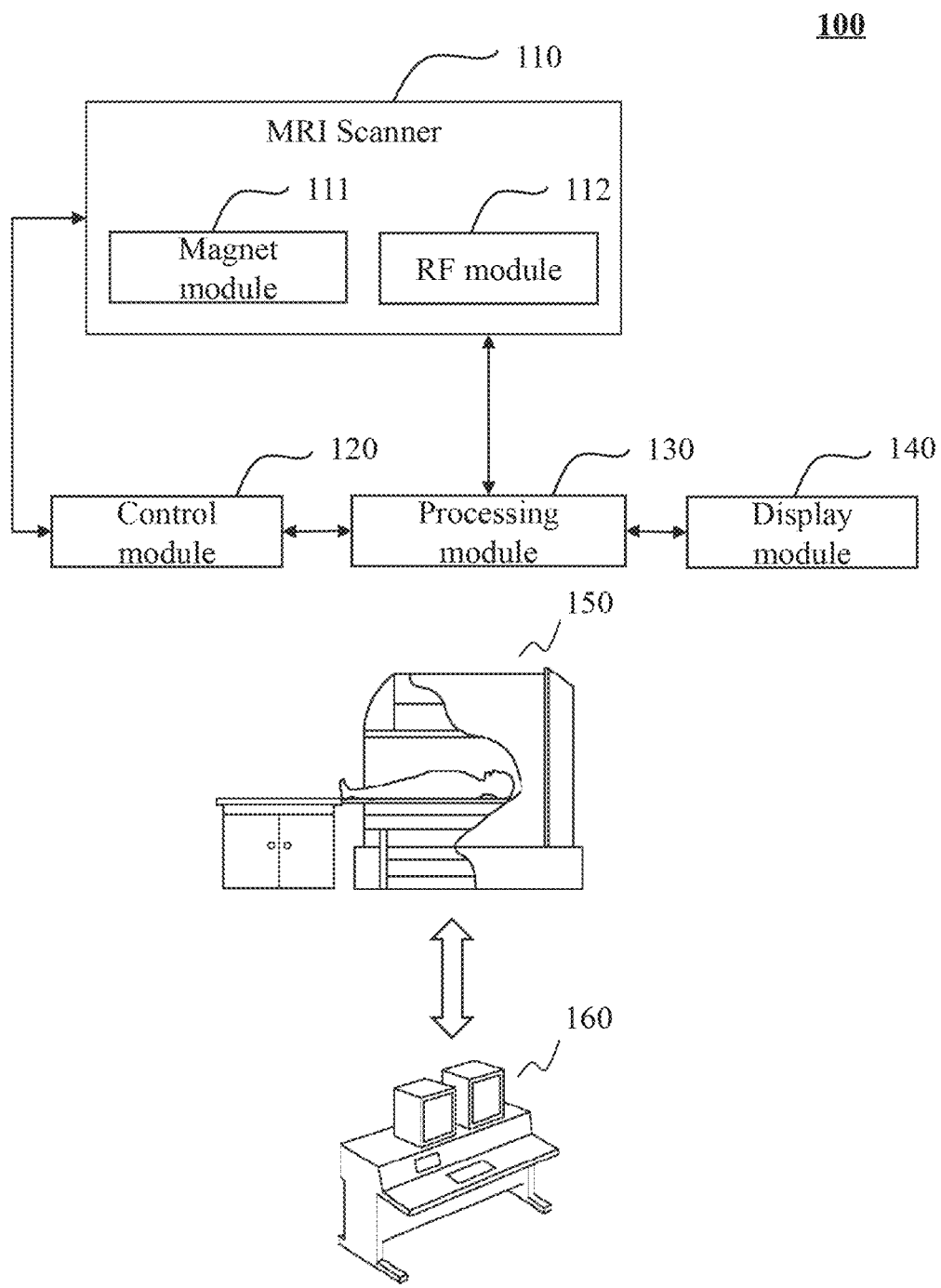
FIG. 1 is a block diagram depicting a magnetic resonance imaging (MRI) system according to some embodiments of the present disclosure.

FIG. 1 is a block diagram of a magnetic resonance imaging system according to some embodiments of the present disclosure. As illustrated, an MRI system 100 may include an MRI scanner 110, a control module 120, a processing module 130, and a display module 140. The MRI scanner 110 may include a magnet module 111 and a radio frequency (RF) module 112. The magnet module 111 may include a main magnet field generator and/or a gradient magnet field generator (not shown in FIG. 1). The main magnet field generator may create a static magnetic field B0 during an MRI process. The main magnet may be of various types including, for example, a permanent magnet, a superconducting electromagnet, a resistive electromagnet, etc. The gradient magnet field generator may generate magnet field gradients to the main magnet field B0 in the X, Y, and/or Z directions. The gradient magnet field may encode the spatial information of a subject located in the MRI scanner 110. The RF module 112 may include RF transmitting coils and/or receiving coils. These RF coils may transmit RF signals to or receive RF signals from a subject of interest. In some embodiments, the function, size, type, geometry, position, amount, and/or magnitude of the magnet module 111 and/or of the RF module 112 may be determined or changed according to one or more specific conditions. For example, according to the difference in function and size, the RF coils may be classified as volume coils and local coils. In some embodiments of the present disclosure, the volume coils may include birdcage coils, transverse electromagnetic coils, surface coils, saddle coils, etc. In some embodiments of the present disclosure, the local coils may include birdcage coils, solenoid coils, saddle coils, flexible coils, etc. In some embodiments, the magnet module 111 and the RF module 112 may be designed to surround a subject to form a tunnel type MRI scanner 150 (i.e. a close-bore MRI scanner), or an open MRI scanner (i.e. an open-bore MRI scanner).

The control module 120 may control the magnet module 111 and/or the RF module 112 of the MRI scanner 110, the processing module 130, and/or the display module 140. The control module 120 may receive information from or send information to the MRI scanner 110, the processing 130, and/or the display module 140. According to some embodiments of the present disclosure, the control module 120 may receive commands from the display module 140 provided by, e.g., a user, and adjust the magnet module 111 and/or RF module 112 to take images of a subject of interest according to the received commands. The processing module 130 may process different kinds of information received from different modules.

For further understanding the present disclosure, several examples are given below, but the examples do not limit the scope of the present disclosure. For example, in some embodiments, the processing module 130 may process MR signals received from the RF module 112 and generate one or more MR images based on these signals and deliver the images to the display module 140. In some embodiments, the processing module 130 may process data input by a user or an operator via the display module 140 and transform the data into specific commands, and supply the commands to the control module 120. The display module 140 may receive input and/or display output information. The input and/or output information may include programs, software, algorithms, data, text, number, images, voice, or the like, or any combination thereof. For example, a user or an operator may input some initial parameters or conditions to initiate a scan. In the present disclosure, user and operator may be used interchangeably unless otherwise stated. As another example, some information may be imported from an external resource, such as a floppy disk, a hard disk, a wireless terminal, or the like, or any combination thereof. In some embodiments, the control module 120, the processing module 130, and/or the display module 140 may be integrated into an MRI console 160. An operator may set parameters in MRI scanning, control the imaging procedure, view the images produced through the MRI console 160.

It should be noted that the above description of the MRI system 100 is merely provided for the purposes of illustration, and not intended to limit the scope of the present disclosure. For persons having ordinary skills in the art, multiple variations and modifications may be made under the teachings of the present disclosure. For example, the assembly and/or function of the MRI system 100 may be varied or changed according to specific implementation scenarios. Merely by way of example, some other components may be added into the MRI system 100, such as a patient positioning module, a gradient amplifier module, and other devices or modules. Note that the MRI system may be a traditional or a single-modality medical system, or a multi-modality system including, e.g., a positron emission tomography-magnetic resonance imaging (PET-MRI) system, a remote medical MRI system, and others, etc. However, those variations and modifications do not depart from the scope of the present disclosure.

Figure 2:
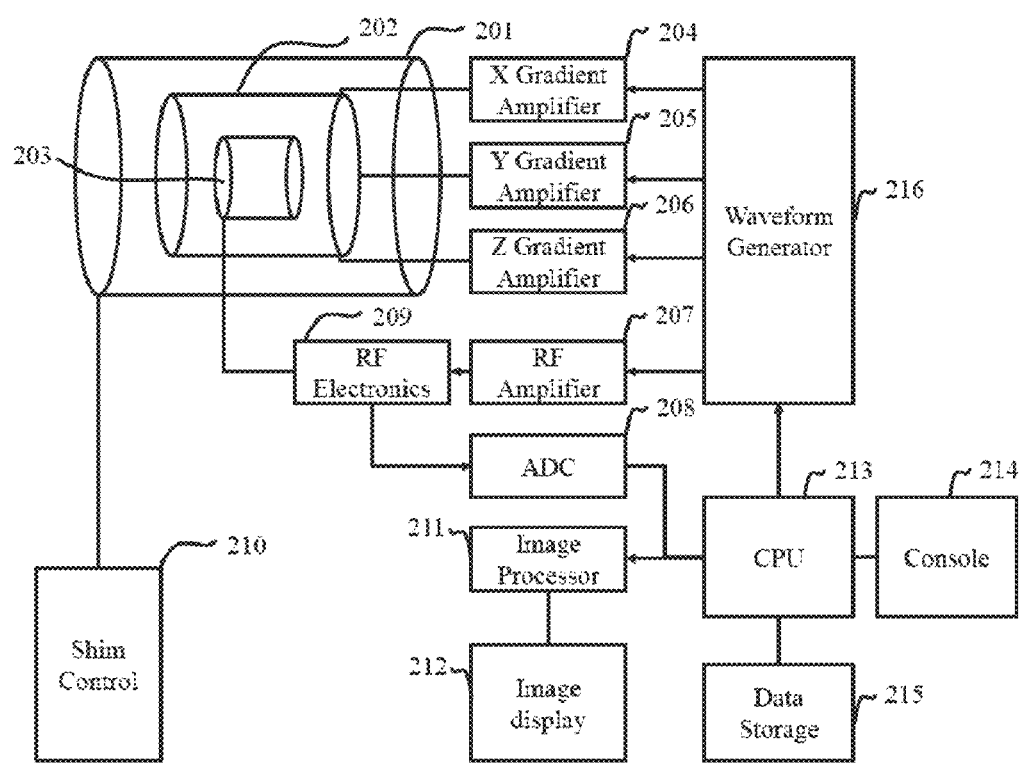
FIG. 2 is a block diagram depicting an MRI system according to some embodiments of the present disclosure.

FIG. 2 is a block diagram of the MRI system 100 according to some embodiments of the present disclosure. As shown in the figure, the main field and shim coils 201 may generate a main magnetic field that may be applied to an object (also referred to as subject) exposed inside the field. The main field and shim coils 201 may also control the homogeneity of the generated main field. Gradient coils 202 may be located inside the main field and shim coils 201. The gradient coils 202 may generate a second magnetic field or referred to as a gradient field. The gradient coils 202 may distort the main field generated by the main field and shim coils 201 so that the magnetic orientations of the protons of an object may vary as a function of their positions inside the gradient field. The gradient coils 202 may include X coils, Y coils, and/or Z coils (not shown in the figure). In some embodiments, the Z coils may be designed based on circular (Maxwell) coils, while the X coils and the Y coils may be designed on the basis of the saddle (Golay) coil configuration. The three sets of coils may generate three different magnetic fields that are used for position encoding. The gradient coils 202 may allow spatial encoding of MR signals for image construction. The gradient coils 202 may be connected with one or more of an X gradient amplifier 204, a Y gradient amplifier 205, or a Z gradient amplifier 206. One or more of the three amplifiers may be connected to a waveform generator 216. The waveform generator 216 may generate gradient waveforms that are applied to the X gradient amplifier 204, the Y gradient amplifier 205, and/or the Z gradient amplifier 206. An amplifier may amplify a waveform. An amplified waveform may be applied to one of the coils in the gradient coils 202 to generate a magnetic field in the X-axis, the Y-axis, or the Z-axis, respectively. The gradient coils 202 may be designed for either a close-bore MRI scanner or an open-bore MRI scanner. In some instances, all three sets of coils of the gradient coils 202 may be energized and three gradient fields may be generated thereby. In some embodiments of the present disclosure, the X coils and Y coils may be energized to generate the gradient fields in the X direction and the Y direction.

RF coils 203 may generate a third magnetic field that is utilized to generate MR signals for image construction. In some instances, the RF coils 203 may include a transmitting coil and a receiving coil. In some embodiments, the RF coils 203 may be in connection with RF electronics 209 that may be configured or used as one or more integrated circuits (ICs) functioning as a waveform transmitter and/or a waveform receiver. The RF electronics 209 may be connected with an RF amplifier 207 and an analog-to-digital converter (ADC) 208. The waveform generator 216 may generate an RF signal. The RF signal may be first amplified by the RF amplifier 207, processed by the RF electronics 209, and applied on the RF coils 203 to generate a third magnetic field, in addition to the magnetic fields generated by, e.g., the main field and shim coils 201 and the gradient coils 202. In some embodiments of the present disclosure, the waveform generator 201 may generate a series of RF waveforms periodically or aperiodically. For instance, the waveform generator 216 may generate an excitation RF pulse with a flip angle of 90° and multiple refocusing RF pulses with a flip angle of 180°. Note that the excitation RF pulse may have a flip angle other than 90°, e.g., any magnitude ranging from 0° to 180°. An excitation RF pulse with a flip angle of 90° is mentioned elsewhere in the present disclosure for illustration purposes, and is not intended to limit the scope of the present disclosure. An excitation RF pulse with a flip angle other than 90° may be used.

As described elsewhere in the present disclosure, the flip angle of a refocusing RF pulse may be of a value other than 180°. Furthermore, the waveform generator 216 may generate a series of RF waveforms periodically or aperiodically. For instance, the waveform generator 216 may generate an excitation RF pulse with a flip angle of 90° and multiple refocusing RF pulses with same flip angles or variable flip angles. The flip angle of the excitation RF pulse may be variable as well. The excitation RF pulse may be utilized to generate the third magnetic field, and with the application of one or more refocusing RF pulses, one or more MR signals may be generated. For instance, an echo train with multiple echoes may be generated. The echo train length (ETL) may be either fixed or variable. For instance, for a same tissue to be imaged, ETL may be fixed. For different tissues, ETL may be variable. Furthermore, even for a same tissue, ETL may be variable. The echo train may be received by the receiving coils of the RF coils 203. Then the echo train may be sent to the RF electronics 209, and transmitted to the ADC 208 for digitization. The echo train may be demodulated and filtered in the electronics 209. Subsequently, the echo train may be processed by an image processor 211, e.g., with the assistance of the CPU 213, to generate one or more images. A console 214 may communicate through a link with the CPU 213 and allow one or more operators to control the production and/or display of images on image display 212. The console 214 may include an input device, a control panel (not shown in the figure), etc. The input device may be a keyboard, a touch screen, a mouse, a remote controller, or the like, or any combination thereof.

The CPU 213 may control the production of the waveforms in the waveform generator 216, and the production of images in the image processor 211. The CPU 213 may be a central processing unit (CPU), an application-specific integrated circuit (ASIC), an application-specific instruction-set processor (ASIP), a graphics processing unit (GPU), a physics processing unit (PPU), a microcontroller unit, a digital signal processor (DSP), a field programmable gate array (FPGA), an ARM, or the like, or any combination thereof.

The data storage 215 may store received MR signals. When an MRI scan is completed and the whole data of a scanned object (e.g., a tissue or a specific part of a body) is acquired. A Fourier transform of the data may be performed by, without limitation to, the CPU 213, the image processor 211, or the like, or any combination thereof. After the transform is completed, one or more desired images may be generated. The images may be stored in the data storage 215. The images may be further conveyed to the image display 212 for display.

In some embodiments, a shim control 210 may be utilized to control the homogeneity of the main magnetic field generated by the main field and shim coils 201.

It should be noted that the above description of the MRI system is merely provided for the purposes of illustration, and not intended to limit the scope of the present disclosure. For persons having ordinary skills in the art, multiple variations and modifications may be made under the teaching of the present invention. However, those variations and modifications do not depart from the scope of the present disclosure.

Figure 3:
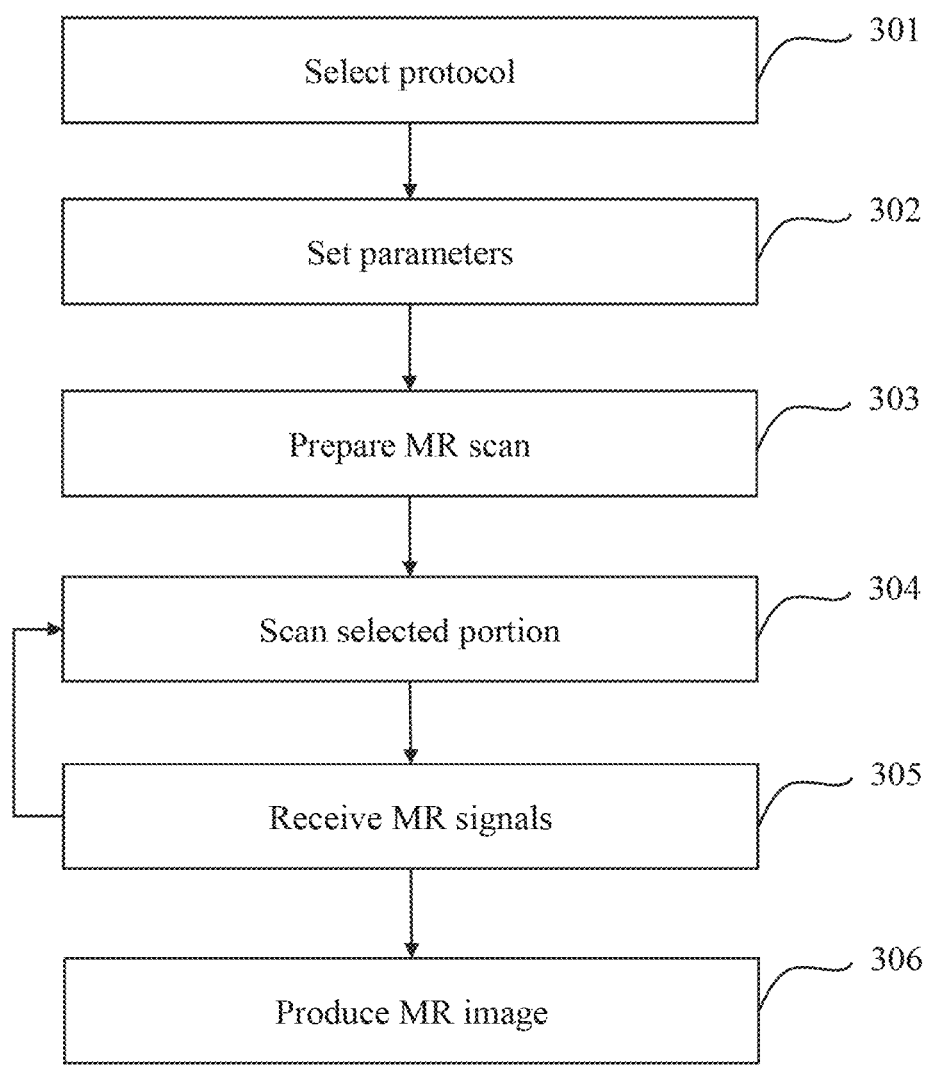
FIG. 3 is a flowchart illustrating a MRI process according to some embodiments of the present disclosure.

FIG. 3 depicts a flowchart of an MR scan that may be performed according to some embodiments of the present disclosure. In step 301, one or more protocols may be selected. A protocol may be designed for imaging one or more tissues, diseases, and/or clinical scenarios. A protocol may contain a certain number of pulse sequences oriented in different planes and/or with different parameters. The pulse sequences may include a spin echo sequence, a gradient echo sequence, a steady state free precession sequence, an inversion recovery sequence, or the like, or any combination thereof. For instance, the spin echo sequences may include fast spin echo (FSE), half-Fourier acquisition single-shot turbo spin-echo (HASTE), turbo gradient spin echo (TGSE), or the like, or any combination thereof. When an MR scan is to be conducted, an operator may select a protocol for the scan. For example, for a cranial scan, the operator may select any one of the protocols called "Routine Adult Brain," "MR Angiogram Circle of Willis," and many others. These protocols described above or other protocols may be stored in the data storage 215 as illustrated in FIG. 2, or other storage devices (e.g., an external storage device or server accessible by the MR system 100).

Parameters may be set in step 302. The parameters may be set via the console 214 through a user interface that may be displayed on, e.g., the image display 212 as specified in FIG. 2. The parameters may include image contrast and/or ratio, a region of interest (ROI), slice thickness, an imaging type (e.g., T1 weighted imaging, T2 weighted imaging, proton density weighted imaging, etc.), T1, T2, a spin echo type (spin echo, fast spin echo (FSE), fast recovery FSE, single shot FSE, gradient recalled echo, fast imaging with steadystate procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), or the like, or any combination thereof.

According to some embodiments of the present disclosure, the term "phase" may refer to a segment, section, part or fragment of a series of flip angles (or a flip angle schedule) corresponding to an echo train divided according to some principles. The number of phase(s) and/or the number of echo(es) in each phase may depend on specific conditions. In some embodiments, an echo train may be divided into several phases according to considerations including, e.g., the characteristics of a reference signal schedule, a desired signal evolution, etc. Merely by way of example, the reference signal schedule of an echo train may be divided into three segments, regardless of what their values are or how their trends vary (e.g. firstly exponential decay, secondly essentially flat, and lastly exponential decay again), then the echo train may be divided into three phases accordingly. In some embodiments, the reference signal schedule may be divided into different phases according to one or more other considerations. For example, only one or several specific echo(es) associated with resultant signal(s) of interest need to be paid attention to. For example, it is desired that the signals corresponding to two echoes meet one or more thresholds; the echo train may belong to a single phase so that the two echoes of interest are located in the same phase; the echo train may be divided into two or more phases, and the two echoes of interest may be located in a same phase or different phases. In some embodiments, there may be no reference signal schedule at all, and the number of phase(s) and/or the number of echo(es) in each phase may be determined based on, e.g., a random division, an equal division, a certain rule, or the like, or any combination thereof. The certain rule may include Arithmetic progression, Geometric progression, Cauchy sequence, Farey sequence, look-and-say sequence, or the like, or a variation thereof, or any combination thereof.

It should be noted that the above description of the MRI system 100 is merely provided for the purposes of illustration, and not intended to limit the scope of the present disclosure. For persons having ordinary skills in the art, multiple variations and modifications may be made under the teachings of the present disclosure. For example, the number of phases in an echo train may be one, two, three, or more, or equal to the number of echoes. In some embodiments, several echoes may be located in one phase, and the remaining echoes belong to one or more other phases or are not assigned to a phase at all. However, those variations and modifications do not depart from the scope of the present disclosure.

Preparation for the MR scan may be performed in step 303. The preparation may include placing an object, e.g., a selected portion of a subject of interest, within the scanning area, setting the scanning range, tuning and matching shimming coils, adjusting a center frequency, adjusting transmitter attenuation/gain, adjusting signal reception attenuation/gain, setting dummy cycles, or the like, or any combination thereof.

The selected portion of a subject of interest may be scanned in step 304. The scanning may include localizer scans, calibration scans for parallel imaging, automatic pre-scan, or the like, or any combination thereof. For instance, the localizer scans may produce localizer images of low resolution and a large field of view (FOV). Such localizer images may be utilized in subsequent steps. In this step, a pulse sequence including, for example, an excitation RF pulse and a series of refocusing RF pulses, may be applied on the selected portion. The flip angles of the refocusing RF pulses may be either fixed or variable.

MRI is a non-invasive imaging technique that uses a powerful main magnet field to align the nucleus spins in a subject (or a portion thereof). When the subject is exposed in a magnetic field (main magnet field B0), the nucleus spins of the subject tend to align with field B0, but may still precess at the Larmor frequency. The overall motion of the nucleus spins in the subject, subject to field B0, may be simplified as net magnetization (M) that is the averaged sum of many individual nucleus spins. The net magnetization M may be broken down into a longitudinal component (along the Z axis, aligned with field B0), and a transverse component (within the XY plane, perpendicular to field B0). With the effect of main magnet field B0, M may constitute a longitudinal magnetization vector in the macroscopic view. A second magnetic field, RF field (field B1), may be applied to M, oscillating at the Larmor frequency, and causing M to precess away from the field B0 direction. During the excitation by an RF field, longitudinal magnetization may decrease and transverse magnetization may appear. Merely by way of example, if an excitation RF pulse with a 90° flip angle is applied, when the RF transmitter is turned off, there is no longitudinal magnetization any more, and only transverse magnetization exists. The transverse magnetization may induce a current signal in the RF receiving coils, and the induced current may be referred to as an MR signal. The MR signal may correspond to one or more echo trains including, for example, one or more echo signals, according to the pulse sequence selected in step 301.

Generated MR signals may be received in step 305. Step 305 may be performed by the RF coils 203 as described in FIG. 2. The MR signals may correspond to one or more echo trains, or the like. It should be noted that step 305 and step 304 may be repeated until sufficient data to generate an image is acquired or an image is generated. One or more operations may be performed on the MR signals to produce images of the selected portion. The operations may further include Fourier transform (FT) of the data, frequency encoding, phase encoding, or the like, or any combination thereof. The operations may include filling data of the MR signals into the Fourier domain (or referred to as the spatial frequency space, or the k-space). For instance, Fourier transform may be a fast Fourier Transform (FFT), a 2-dimensional FT, a 3-dimensional FT, or the like, or any combination thereof. In step 306, one or more images of the selected portion may be produced. The images may be displayed on, e.g., the image display 212 (shown in FIG. 2), or other display devices (e.g., an external display device).

It should be noted that the flowchart described above is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. For instance, step 301, step 302, and step 303 may be performed sequentially in an order other than that described above in connection with FIG. 3. Alternatively, step 301, step 302, and step 303 may be performed concurrently.

FIG. 4-A is a block diagram illustrating an architecture of a processing module according to some embodiments of the present disclosure. In some embodiments, the processing module 130 may include a CPU. The CPU may be a central processing unit (CPU), an application-specific integrated circuit (ASIC), an application-specific instruction-set processor (ASIP), a graphics processing unit (GPU), a physics processing unit (PPU), a microcontroller unit, a digital signal processor (DSP), a field programmable gate array (FPGA), an ARM, or the like, or any combination thereof. As illustrated in FIG. 4-A, the processing module 130 may include an acquisition unit 402, a magnitude processing unit 404, a phase processing unit 406 and an image generating unit 408. The units may be connected or otherwise communicate with each other via a wired connection (e.g., a metal cable, an optical cable, a hybrid cable, or the like, or any combination thereof) or a wireless connection (e.g., a Local Area Network (LAN), a Wide Area Network (WAN), a Bluetooth, a ZigBee, a Near Field Communication (NFC), or the like, or any combination thereof).

The acquisition unit 402 may acquire echo signals. The echo signals may be acquired from the MRI scanner 110 or any storage disclosed anywhere in the present disclosure. In some embodiments, the echo signals may be spatially encoded. For example, a phase encoding gradient and a frequency encoding gradient may be applied. As another example, a slice selection gradient may be imposed along an axis perpendicular to the plane of the desired slice, resulting in a linear variation of potential resonance frequencies in that direction. In some embodiments, a plurality of echo signals or a single-echo signal may be acquired. In some embodiments, the acquisition unit 402 may include an A/D converter (not shown in FIG. 4-A). The acquired echo signals may be converted from analog signals to digital signals.

The magnitude processing unit 404 may process the magnitude information. In some embodiments, the magnitude information may be processed, e.g., extracted, calculated, or the like, or a combination thereof. In some embodiments, the magnitude processing unit 404 may generate one or more original magnitude images, compute a magnitude map, a T2* magnitude map, a R2* (R2*=1/T2*) magnitude map, or a T2* mask. In some embodiments, the original magnitude images may be generated based on the magnitude information of the echo signals. An echo signal may include magnitude information and phase information. The echo signals may be filled into the k-space, and the magnitude information of the echo signals may be extracted and may be used to reconstruct one or more original magnitude images based on Fourier transform. In some embodiments, an original magnitude image may correspond to an echo signal. For example, if a single-echo signal is acquired, only one set of original magnitude images corresponding to a specific echo time may be generated. As another example, multiple sets of original magnitude images may be generated based on a plurality of echo signals corresponding to different echo times. In some embodiments, based on the original magnitude images, a magnitude map including, e.g., a virtual magnitude map, an average magnitude map, a T2* magnitude map, or a R2* magnitude map may be generated. In some embodiments, a T2* mask may be generated based on a T2* magnitude map.

The phase processing unit 406 may process the phase information. In some embodiments, the phase information may be processed, e.g., extracted, calculated, unwrapped, filtered, or the like, or a combination thereof. In some embodiments, the phase processing unit 406 may generate one or more original phase images, process the one or more original phase images, and/or compute a virtual phase map or a phase mask. In some embodiments, the phase processing unit 406 may generate one or more original phase images based on the phase information of the echo signals. As mentioned above, the echo signals may be filled into the k-space. The phase information of the echo signals may be extracted and may be used to reconstruct one or more original phase images based on Fourier transform. In some embodiments, an original phase image may correspond to an echo signal. For example, if a single-echo signal is acquired, only one set of original phase images corresponding to the same echo time may be generated. As another example, multiple sets of original phase images may be generated based on a plurality of echo signals corresponding to different echo times.

In some embodiments, the original phase images may be processed to remove or reduce the effect of one or more interference factors (e.g., a phase wrap-around artifact, a background field, or the like) on the phase information, to generate a processed phase image. In some embodiments, the process of reducing or removing the effect of one or more interference factors on the phase information may include a process of phase unwrapping (also referred to as "phase unwrapping correction") and/or a process of background field removal. The process of phase unwrapping may be performed to reduce or remove phase wrap-around artifact in the original phase image. An unwrapped phase map may be generated based on the phase unwrapping correction. The process of background field removal may be performed to reduce or remove the effect of the background field on the phase information. In some embodiments, the processed phase image may be a phase image with the phase wrap-around artifact removed or reduced (also referred to as a "corrected phase image"), a phase image with the background field removed or reduced, or a phase image with both the phase wrap-around artifact and the background field removed or reduced.

In some embodiments, the process of phase unwrapping and the process of background field removal may be performed simultaneously or successively. For example, the process of phase unwrapping may be performed first and the process of background field removal may be performed later. In some embodiments, the process of background field removal may be unnecessary. In some embodiments, one of the process of phase unwrapping and the process of background field removal may be performed.

In some embodiments, a virtual phase map may be generated based on the processed phase images (e.g., the processed phase images with the phase wrap-around artifacts removed or reduced). In some embodiments, a phase mask may be determined based on the processed phase images or the virtual phase map.

The image generating unit 408 may generate an image based on the echo signals acquired by the acquisition unit 402, the magnitude information processed by the magnitude processing unit 404, and/or the phase information processed by the phase processing unit 406. In some embodiments, the image generating unit 408 may spatially decode an MR signal (also referred to as an echo signal) that has been spatially encoded by the magnetic field(s). In some embodiments, the image generating unit 408 may generate a magnitude image and/or a phase image based on the acquired echo signals. In some embodiments, the imaging generating unit 408 may generate a susceptibility weighted image according to a susceptibility weighted imaging (SWI) method. The susceptibility weighted image may be generated based on the magnitude information and the phase information. In some embodiments, the image generating unit 408 may employ different kinds of imaging reconstruction techniques for the image reconstruction procedure. Exemplary image reconstruction techniques may include Fourier reconstruction, constrained image reconstruction, regularized image reconstruction in parallel MRI, or the like, or a variation thereof, or any combination thereof.

It should be noted that the above description of the processing module 130 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the magnitude processing unit 404 and the phase processing unit 406 may be integrated in an independent module or unit used to process both the magnitude information and the phase information. As another example, the processing module 130 may further include a storage unit (not shown). The storage unit may be used to store the acquired echo signals and/or any intermediate data generated during any process performed by any unit in the processing module 130. As a further example, the units in the processing module 130 may include a storage block respectively, or the units may share a common storage block.

FIG. 4-B is a flowchart illustrating a process for generating a susceptibility weighted image according to some embodiments of the present disclosure. In step 420, echo signals may be acquired. In some embodiments, a gradient echo (GRE) sequence may be applied to acquire echo signals. In some embodiments, the gradient echo sequence may be a single gradient echo sequence or a multi echo gradient echo sequence. In some embodiments, a plurality of echo signals or a single echo signal may be acquired. The plurality of echo signals may be acquired from a multi-echo gradient echo sequence. In some embodiments, the echo signals acquired from the multi-echo gradient echo sequence may be equidistant or non-equidistant. As used herein, the term "equidistant" may refer to that the interecho spacing ($\Delta TE$) between two adjacent echoes (e.g., echo 711 and echo 712 described in FIG. 7-A) may be equal. The term "non-equidistant" may refer to that the interecho spacing ($\Delta TE$) between two adjacent echoes may be unequal. For example, if there are 4 echoes in a repetition time acquired from the multi-echo gradient echo sequence, the echo time of the first echo may be 5 milliseconds, the echo time of the second echo may be 10 milliseconds, the echo time of the third echo may be 15 milliseconds, and the echo time of the fourth echo may be 20 milliseconds. The interecho spacing between any two adjacent echoes may be the same (5 milliseconds). Herein the 4 echoes may be equidistant. As another example, if there are 4 echoes in a repetition time acquired from the multi-echo gradient echo sequence, the echo time of the first echo may be 5 milliseconds, the echo time of the second echo may be 12 milliseconds, the echo time of the third echo may be 20 milliseconds, and the echo time of the fourth echo may be 25 milliseconds. The interecho spacing between the first echo and the second echo may be 7 milliseconds, the interecho spacing between the second echo and the third echo may be 8 milliseconds, and the interecho spacing between the third echo and the fourth echo may be 5 milliseconds. Herein the 4 echoes may be non-equidistant. In some embodiments, the gradient echo sequence may be a two-dimensional (2D) gradient echo sequence or a three-dimensional (3D) gradient echo sequence. In some embodiments, the gradient echo sequence may include a GRE-echo planar imaging (GRE-EPI) sequence or a multi-echo GRE (ME-GRE) (more detailed description regarding the gradient echo sequence may be found in FIG. 7-A and FIG. 7-B).

In some embodiments, a phase encoding gradient and a frequency encoding gradient (also referred to as "readout gradient") may be applied to encode the echo signals. A readout gradient may be imposed along the readout gradient direction. In some embodiments, for the gradient echo sequence, the readout gradient may be used to generate echo signals by a gradient reversal. In some embodiments, for a multi-echo gradient echo sequence, the readout gradient may be bipolar or monopolar. As used herein, if the polarities of the readout gradients imposed on two adjacent echoes are opposite, the readout gradients may be referred to as bipolar readout gradients. If the polarities of the readout gradients imposed on two adjacent echoes are the same, the readout gradients may be referred to as monopolar readout gradients. In some embodiments, when using the monopolar readout gradient, a fly back gradient may be inserted between any two adjacent readout gradients. As used herein, the fly back gradient may have a polarity opposite to the polarity of the monopolar gradient, so that the echo signals may be generated (more details regarding the readout gradient may be found in FIG. 7-A and FIG. 7-B).

In some embodiments, a flow compensation may be performed. For a static tissue, the accumulated phase along the slice selection direction, the phase encoding direction, and/or the readout direction after the acquisition process may be zero. For a tissue, for example, blood, because of the flow or motion, there may be accumulated phase along the slice selection direction, the phase encoding direction, or the readout direction after the acquisition process, which may lead to a reduction or attenuation of the echo signals and/or the occurrence of artifacts in the image.

Merely by way of example, the magnitude information and/or phase information of the echo signals acquired from a region near an artery may be affected due to the blood flow. In a reconstructed susceptibility weighted image, image information corresponding to the signals acquired from the region near an artery may be low, and it may be difficult to make a distinction with the image information corresponding to the signals acquired from a region near a vein. A flow compensation may be performed to reduce the effect of blood flow on an image. In some embodiments, a gradient parameter may be adjusted during the flow compensation process so that the first moment of the gradient equals approximately 0 at the time corresponding to the center of the echo. As used herein, "approximately" describing a numerical value, a parameter, or a characteristic may indicate that the variation is within 2%, or 5%, or 8%, or 10%, or 15%, or 20% of the numerical value, the parameter, or the characteristic. The gradient parameter may include gradient amplitude, gradient duration, starting time of the gradient along the direction of the blood flow, or the like, or a combination thereof. The flow compensation may improve, in a magnitude image, the magnitude information corresponding to the signals acquired from the region near an artery. The flow compensation may reduce or remove erroneous phase information from the phase image. In a susceptibility weighted image generated based on the magnitude image and the phase image improved by the flow compensation, the image information corresponding to the region near an artery may be improved or enhanced, and it may be easy to distinguish the image information with the image information corresponding to the region near an vein. The flow compensation may be applied to reduce the effect of a motion other than blood flow, e.g., cerebrospinal fluid (CSF), breathing, heartbeat, or gastrointestinal motility, or the like, on an image.

In some embodiments, the flow compensation may be performed along the slice selection direction, the readout direction (i.e., the frequency encoding direction), and/or the phase encoding direction. In some embodiments, for the flow compensation along the readout direction, the flow compensation may be performed such that the zeroth moment of the readout gradients equals approximately 0 and an echo may be generated. The first moment of the readout gradients may be equal to approximately 0 at the time of the center of the echo and the amount of the accumulated phase along the readout gradient may be reduced or removed.

In some embodiments, for a multi-echo gradient echo sequence, an additional gradient lobe may be introduced or not during the flow compensation. For example, when an additional gradient lobe is applied, for the echo signals acquired with bipolar readout gradients, the flow compensation is applied to the odd echo signals but not the even echo signals; for the echo signals acquired with monopolar readout gradients, the flow compensation is applied to the first echo signal but not the other echo signals. When no additional gradient lobe is applied, for the echo signals acquired with bipolar readout gradients, the flow compensation is applied to the even echo signals but not the odd echo signals; for the echo signals acquired with monopolar readout gradients, no flow compensation is applied to the echo signals.

In some embodiments, for the flow compensation along the phase encoding direction, the flow compensation may be performed to make the zeroth moment and the first moment of the phase encoding gradients satisfy Equation (1) and Equation (2) below:

$$M_0(0) \equiv \int_{-\infty}^{0} \Delta G_y(t)dt = \frac{1}{\gamma' L_y}, \quad \text{Equation (1)}$$

and $$M_1(0) \equiv \int_{-\infty}^{0} t\Delta G_y(t)dt = 0, \quad \text{Equation (2)}$$

where t may refer to the time relative to the time origin at the echo time, $\Delta G_y(t)$ may represent the phase encoding gradient, $M_0(0)$ may represent the zeroth moment of the phase encoding gradient $\Delta G_y(t)$, $M_1(0)$ may represent the first moment of the phase encoding gradient $\Delta G_y(t)$, $L_y$ may represent the distance of a field-of-view (FOV) along the phase encoding direction, $\gamma'$ may represent a constant relating to $\gamma$, $\gamma$ may represent the gyromagnetic ratio of the proton. The relationship between $\gamma'$ and $\gamma$ may be represented by Equation (3) below:

$$\gamma'=\gamma/(2\pi). \quad \text{Equation (3)}$$

Therefore, the flow compensation along the phase encoding direction may be performed based on equation (1) and equation (2) with respect to the specified echo time.

In step 440, phase information may be processed. The phase information may be derived from the echo signals acquired in step 420. In some embodiments, one or more original phase images may be generated based on the phase information of the echo signals. In some embodiments, the original phase image may be processed to reduce or remove the effect of one or more interference factors (e.g., phase wrap-around artifact, background field, or the like) on the phase information, to generate the processed phase image. In some embodiments, the process of reducing or removing the effect of one or more interference factors on the phase information may include a process of phase unwrapping and/or a process of background field removal. The process of phase unwrapping may be performed to reduce or remove phase wrap-around artifact in the original phase image. An unwrapped phase map may be generated based on the phase unwrapping correction. The process of background field removal may be performed to reduce or remove the effect of the background field on the phase information. In some embodiments, the processed phase image may be a phase image with the phase wrap-around artifact removed or reduced, a phase image with the background field removed or reduced, or a phase image with both the phase wrap-around artifact and the background field removed or reduced. In some embodiments, a virtual phase map may be generated based on the processed phase images. For example, a virtual phase map may be generated based on the processed phase images with the phase wrap-around artifact removed or reduced. In some embodiments, a phase mask may be computed based on the processed phase images or the virtual phase map.

In step 460, magnitude information may be processed. The magnitude information may be derived from the echo signals acquired in step 420. In some embodiments, one or more original magnitude images may be generated based on the magnitude information. In some embodiments, the magnitude information may be analyzed and/or computed, and a T2* magnitude map (or a R2* magnitude map, wherein R2*=1/T2*), a virtual magnitude map, and/or an average magnitude map may be generated. In some embodiments, a T2* mask may be generated based on the T2* magnitude map.

In step 480, a susceptibility weighted image may be generated. In some embodiments, the susceptibility weighted image may be generated based on the magnitude information and/or the phase information.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the processing the phase information and the processing the magnitude information may be performed simultaneously or successively. As another example, a storing step or a caching step may be added between any two steps, in which signals or intermediate data may be stored or cached.

Figure 5:
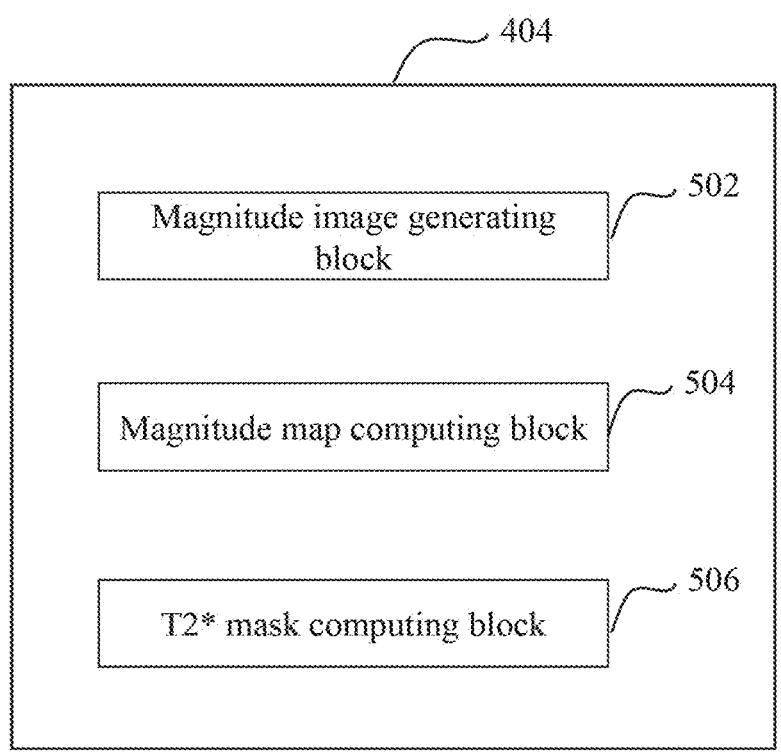
FIG. 5 is a block diagram illustrating an architecture of a magnitude processing unit according to some embodiments of the present disclosure.

FIG. 5 is a block diagram illustrating an architecture of a magnitude processing unit according to some embodiments of the present disclosure. The magnitude processing unit 404 may include a magnitude image generating block 502, a magnitude map computing block 504, and a T2* mask computing block 506.

The magnitude image generating block 502 may generate one or more original magnitude images based on echo signals. The magnitude image generating block 502 may receive echo signals from the acquisition unit 402. The method of generating the original magnitude image may include single channel imaging, or multi-channel imaging. In some embodiments, if the k-space is sufficiently or fully sampled, exemplary algorithms of the multi-channel imaging used to generate the original magnitude image may include Sum of Square (SOS), Adaptive Coil Combine (ACC), or the like, or any combination thereof. If the k-space is under-sampled, exemplary algorithms of the multi-channel imaging used to generate the original magnitude image may include Sensitivity Encoding (SENSE), Simultaneous Acquisition of Spatial Harmonics (SMASH), Generalized Auto-calibrating Partially Parallel Acquisition (GRAPPA), or the like, or the combination thereof. In some embodiments, an original magnitude image may correspond to an echo signal. For example, if a single-echo signal is acquired, for single channel imaging, only one original magnitude image may be generated. As another example, a plurality of original magnitude images may be generated based on a plurality of echo signals corresponding to different echo times.

The magnitude map computing block 504 may compute one or more magnitude maps based on the original magnitude images and/or the magnitude information. In some embodiments, the magnitude map computing block 504 may receive the original magnitude images from the magnitude image generating block 502. In some embodiments, in the magnitude map, the T2* weighted information may be enhanced. In some embodiments, the magnitude map may include a virtual magnitude map, an average magnitude map, or a T2* magnitude map. As used herein, a virtual magnitude map may refer to a map generated based on a set of virtual magnitude information calculated based on a virtual echo time and original magnitude information. An average magnitude map may refer to a map including the weighted average of a plurality of magnitude images corresponding to different echo times. A T2* magnitude map may refer to a map generated based on a set of T2* information. As used herein, T2* may be defined as a time constant for the decay of transverse magnetization arising from natural interactions at the atomic or molecular levels within the tissue or substance of interest and inhomogeneities in the main magnetic field. In some embodiments, the decay above may be represented by R2* that has a reciprocal relationship with T2*.

In some embodiments, the magnitude map computing block 504 may include a virtual magnitude map computing block (not shown), an average magnitude map computing block (not shown), or a T2* magnitude map computing block (not shown), used to generate a virtual magnitude map, an average magnitude map, and a T2* magnitude map, respectively. In some embodiments, the procedure of computing the virtual magnitude or the value of T2* at a pixel location corresponding to an echo time may include a process of estimating the value of a variable (e.g., the virtual magnitude) on the basis of its relationship with another variable (e.g., the echo time, etc.). In some embodiments, the relationship may be obtained by fitting a continuity equation or a discrete equation. Theoretically, the more the data points (e.g., magnitude information corresponding to different echo times) are, the more accurate the fitting result may be. In some embodiments, the number of the data points needed for fitting may range from 2 to 20. In some embodiments, the fitting method may include interpolation, extrapolation, smoothing, regression analysis, the least square method, or the like, or any combination thereof. Exemplary interpolation methods may include Lagrange interpolation, Newton interpolation, Hermite interpolation, piecewise interpolation, spline interpolation, linear interpolation, or the like, or a combination thereof. Exemplary extrapolation methods may include linear extrapolation, polynomial extrapolation, conic extrapolation, French curve extrapolation, or the like, or a combination thereof. Exemplary regression analysis may include linear regression, nonlinear regression, multiple regression, logistic regression, partial regression, or the like, or a combination thereof. As an example, an exponential equation may be fitted and used to compute the value of the T2* and/or the virtual magnitude at a pixel location corresponding to an echo time (see details in FIG. 8-A).

The T2* mask computing block 506 may compute a T2* mask based on the magnitude map (e.g., the T2* magnitude map). In the T2* mask, the contrast of the magnitude information may be enhanced. For example, the T2* mask may multiply an original magnitude image or a magnitude map (e.g., a virtual magnitude map), and the contrast of the original magnitude image or the magnitude map may be enhanced. As another example, the T2* mask may be combined with a phase mask, and a weighted mask may be generated. The weighted mask may be further used to multiply a magnitude image or magnitude map (e.g., a virtual magnitude map) to generate a susceptibility weighted image.

In some embodiments, the magnitude image generating block 502, the magnitude map computing block 504 and the T2* mask computing block 506 may be connected or otherwise communicate with each other via a wired connection (e.g., a metal cable, an optical cable, a hybrid cable, or the like, or any combination thereof) or a wireless connection (e.g., a Local Area Network (LAN), a Wide Area Network (WAN), a Bluetooth, a ZigBee, a Near Field Communication (NFC), or the like, or any combination thereof). For example, the T2* mask computing block 506 may receive the magnitude map (e.g., T2* magnitude map) from the magnitude map computing block 504. In some embodiments, the blocks in the magnitude processing unit 404 may communicate with other units (e.g., the image generating unit 408). For example, the T2* mask computing block 506 may send the T2* mask to the image generating unit 408 for further use In some embodiments, the magnitude processing unit 404 may further include one or more storage blocks. The storage block may store data generated by the magnitude image generating block 502, the magnitude map computing block 504, or the T2* mask computing block 506. The blocks in the magnitude processing unit 404 may communicate with the storage blocks in real time, or within a specific time interval.

It should be noted that the above description of the magnitude processing unit is merely provided for the purposes of illustration, and not intended to limit the scope of the present disclosure. For persons having ordinary skills in the art, multiple variations or modifications may be made under the teachings of the present disclosure. For example, the assembly and/or function of the magnitude processing unit 404 may be varied or changed. In some embodiments, the magnitude image generating block 502, the magnitude map computing block 504, and the T2* mask computing block 506 may share one storage block. In some embodiments, the magnitude image generating block 502, the magnitude map computing block 504, and the T2* mask computing block 506 may have their own storage blocks, respectively. In some embodiments, the T2* mask computing block 506 or the magnitude map computing block 504 may be unnecessary. However, those variations and modifications do not depart from the scope of the present disclosure.

FIG. 6-A is a block diagram illustrating an architecture of a phase processing unit according to some embodiments of the present disclosure. The phase processing unit 406 may include a phase image generating block 602, a phase information processing block 604, a virtual phase computing block 606, and a phase mask computing block 608.

The phase image generating block 602 may generate one or more original phase images based on echo signals. In some embodiments, the phase image generating block 602 may receive the echo signals from the acquisition unit 402. The method of generating the original phase image may include single channel imaging, or multi-channel imaging. In some embodiments, the algorithm of the multi-channel imaging used to generate the phase image may include the weighted average method, the adaptive coil combine (ACC) algorithm, the method of performing zero-order phase correction to the other channels relative to a reference channel and then performing multi-channel combination, or the like, or any combination thereof. Descriptions regarding the weighted average method may be found in, for example, Hammond et al., Neuroimage, 39: 1682-1692 (2008), which is hereby incorporated by reference. In some embodiments, an original phase image may correspond to an echo signal. For example, if a single-echo signal is acquired, only one original phase image may be generated. As another example, a plurality of original phase images may be generated based on a plurality of echo signals corresponding to different echo times.

The phase information processing block 604 may process the original phase information in the original phase image, to generate a processed phase image. In some embodiments, the phase information processing block 604 may include a phase unwrapping block (not shown) and a background field processing block (not shown). The phase unwrapping block may reduce or remove phase wrap-around artifacts in an original phase image. As used herein, a phase wrap may refer to the phase that is wrapped in an interval of a $2\pi$ (e.g., $(-\pi, \pi]$). Exemplary methods used to reduce or remove phase wrap-around artifacts may include the phase unwrapping algorithm based on a single-echo sequence or a multi-echo sequence. Descriptions regarding the algorithm based on a multi-echo sequence may be found in, for example, Feng et al., Magnetic Resonance in Medicine, 70(1): 117-126 (2013), which is hereby incorporated by reference. Descriptions regarding the algorithm based on a single-echo sequence may be found in, for example, Abdul-Rahman et al., Applied Optics, 46(26): 6623-6635 (2007), which is hereby incorporated by reference. In some embodiments, the phase unwrapping algorithm based on a single-echo sequence may include a global error-minimization method (e.g., the least-square algorithm, etc.), a residue-balancing method, a quality-guided algorithm, or the like, or a combination thereof.

The background field processing block may reduce or remove the effect of the background field on the phase information. In some embodiments, the background field may be caused by the inhomogeneity of the main magnetic field. Exemplary methods used to remove the background field may include Sophisticated Harmonic Artifact Reduction for Phase data (SHARP). Descriptions regarding SHARP may be found in, for example, Schweser et al., NeuroImage, 54(4): 2789-2807 (2011), which is hereby incorporated by reference.

In some embodiments, the processed phase image may be a phase image with the phase wrap-around artifact removed or reduced, a phase image with the background field removed or reduced, or a phase image with both the phase wrap-around artifact and the background field removed or reduced.

The virtual phase computing block 606 may compute a virtual phase based on the processed phase image (e.g., a processed phase image with the phase wrap-around artifacts removed or reduced). In some embodiments, a virtual phase map may be generated based on the virtual phase and the processed phase images. In some embodiments, during an MR process, in the region of interest (ROI) of an object, the susceptibilities of different tissues may be different, and the tissues with different susceptibilities in the image may present different contrasts according to different echo times. For example, for a small tissue or organ (e.g., a small vein, etc.) or a tissue with a weak susceptibility (e.g., basal ganglia, etc.), a long echo time (e.g., TE=20 milliseconds at 3T) may be selected and the contrast of the tissue or organ presented in the susceptibility weighted image may be sufficiently enhanced. For a tissue with a strong susceptibility (e.g., a hemorrhagic spot, etc.), a phase wrap-around artifact may occur, and therefore a short echo time (e.g., TE=10 milliseconds as 3T) may be suitable. Therefore, different tissues or organs may correspond to different echo times in order to obtain a desired image contrast. In some embodiments, during the acquisition process, a plurality of echo signals may be acquired. The plurality of echo signals (also referred to as "echoes") may correspond to a number of discrete echo times. As used herein, "discrete" may refer to that the echo times may be discontinuous and there may be a specific time interval (also referred to as "$\Delta$ TE between two adjacent echoes", see details in FIG. 4-B) between any two adjacent echo times. In some embodiments, a virtual phase may be computed based on a virtual echo time. The virtual echo time may be selected based on a default setting of the imaging system 100, or based on instructions from an operator (e.g., a doctor). In some embodiments, the virtual echo time may be selected within a time interval between any adjacent discrete echo times. A virtual phase map may be generated based on the virtual phase and the original phase information. The virtual phase map may be used to obtain a desired image contrast instead of actually acquiring corresponding echo signal(s). In some embodiments, a plurality of virtual phases corresponding to a plurality of virtual echo times may be computed. The virtual echo time may be any positive number. The number of the virtual echo times may be any positive number.

The phase mask computing block 608 may compute a phase mask based on the virtual phase map or the processed phase image. In some embodiments, the phase mask may be used to enhance the contrast of the original magnitude image or the magnitude map. For example, the phase mask may multiply with a magnitude image or a magnitude map (e.g., a virtual magnitude map), and the contrast of the original magnitude image or the magnitude map may be enhanced. As another example, the phase mask may be combined with the T2* mask, and a weighted mask may be generated. The weighted mask may be further used to multiply a magnitude image or magnitude map (e.g., a virtual magnitude map) to generate a susceptibility weighted image.

In some embodiments, different phase masks may be used under different conditions including, e.g., the characteristic of a tissues of interest (e.g., paramagnetism or diamagnetism), the characteristic of a coordinate system (e.g., the right-handed coordinate system or the left-handed coordinate system), or the like, or a combination thereof. As used herein, paramagnetism may refer to a form of magnetism whereby a material may be attracted by an externally applied magnetic field and form an internal induced magnetic field in the same direction as the applied magnetic field. In contrast, a diamagnetic material may be repelled by a magnetic field and form an induced magnetic field in the direction opposite to that of the applied magnetic field. For instance, a paramagnetic object may include a hemorrhagic spot, a tissue of iron accumulation, or the like. A diamagnetic object may include a tissue of calcification (e.g., bone, tooth, etc.), a tissue with pathological calcification (e.g., an intracranial calcification, etc.), or the like.

In some embodiments, the units in the phase processing unit 406 may be connected with each other via a wired connection or a wireless connection. For example, the phase information processing block 604 may receive the original phase image from the phase image generation block 602. As another example, the phase information processing block 604 may send the processed phase image to the virtual phase computing block 606, and/or the phase mask computing block 608.

In some embodiments, the phase processing unit 406 may further include one or more storage blocks. The storage block may store data generated by the phase image generating block 602, the phase information processing block 604, the virtual phase computing block 606, or the phase mask computing block 608. The blocks in the phase processing unit 406 may communicate with the storage blocks in real time, or within a specific time interval.

It should be noted that the above description of the phase processing unit is merely provided for the purposes of illustration, and not intended to limit the scope of the present disclosure. For persons having ordinary skills in the art, multiple variations or modifications may be made under the teachings of the present disclosure. For example, the assembly and/or function of the phase processing unit 406 may be varied or changed. In some embodiments, the phase image generating block 602, the phase information processing block 604, the virtual phase computing block 606 and the phase mask computing block 608 may share one storage block. In some embodiments, the phase image generating block 602, the phase information processing block 604, the virtual phase computing block 606, and the phase mask computing block 608 may have their own storage blocks, respectively. In some embodiments, the virtual phase computing block 606 may be unnecessary. In some embodiments, the background field processing block (not shown) may be unnecessary. However, those variations and modifications do not depart from the scope of the present disclosure.

FIG. 6-B is a flowchart illustrating a process for obtaining a phase mask according to some embodiments of the present disclosure. In step 610, one or more original phase images may be generated based on echo signals. The generation of the original phase image may be performed by the phase image generating block 602. In some embodiments, an original phase image may correspond to an echo signal. For example, if a single-echo signal is acquired, only one set of original phase images corresponding to the same echo time may be generated. As another example, multiple sets of original phase images may be generated based on a plurality of echo signals corresponding to different echo times. In some embodiments, the method of generating an original phase image may include single channel imaging, or multi-channel imaging. In some embodiments, the algorithm of the multi-channel imaging may include the weighted average method, the adaptive coil combine (ACC) algorithm, the method of performing zero-order phase correction to the other channels relative to a reference channel and then performing multi-channel combination, or the like, or any combination thereof. Descriptions regarding the weighted average method may be found in, for example, Hammond et al., Neuroimage, 39): 1682-1692 (2008), which is hereby incorporated by reference.

In step 620, the original phase information in the original phase image may be processed to generate a processed phase image. The process for processing the original phase information may be performed by the phase information processing block 604.

In some embodiments, the original phase image may reflect the spatial distribution of the field incorrectly or inaccurately because of the effect of one or more interference factors (e.g., phase wrap-around artifact, background field, noise, or the like), which may interfere with the generation of the virtual phase map and the determination of the phase mask. The original phase image may be processed to reduce or remove the effect of the interference factors.

In some embodiments, the processing the original phase information may include phase unwrapping and/or background field removal. In some embodiments, the original phase information may be obtained from MR complex signals using, for example, the inverse trigonometric function. Therefore, the original phase information may be normally wrapped in an interval of which the value is $2\pi$ (e.g., $(-\pi, \pi)$). The wrapped phase may lead to a phase wrap-around artifact. Because the inverse trigonometric function has the characteristic expressed as $f(\emptyset+2\pi)=f(\emptyset)$, the procedure of phase unwrapping may be carried out by either adding or subtracting an integer times of $2\pi$ to all successive pixels. In some embodiments, the phase unwrapping algorithm may include an algorithm based on a single-echo sequence and the algorithm based on a multi-echo sequence. Descriptions regarding the algorithm based on a multi-echo sequence may be found in, for example, Feng et al., Magnetic Resonance in Medicine, 70(1): 117-126 (2013), which is hereby incorporated by reference. Descriptions regarding the algorithm based on a single-echo sequence may be found in, for example, Abdul-Rahman et al., Applied Optics, 46(26): 6623-6635 (2007), which is hereby incorporated by reference. In some embodiments, the algorithm based on a single-echo sequence may include a global error-minimization method (e.g., the least-square algorithm), a residue-balancing method, a quality-guided algorithm, or the like.

In some embodiments, the background field may be caused by the inhomogeneity of the main field. In some embodiments, the method of removing background field may include SHARP as described in Schweser et al., NeuroImage, 54(4): 2789-2807 (2011), which is hereby incorporated by reference.

In some embodiments, the process of phase unwrapping and the process of background removal may be performed simultaneously or successively. Exemplary algorithms used to remove the phase wrap-around artifact and the background field simultaneously may include Projection onto Dipole Field, high pass filtering, or the like, or any combination thereof. For example, high pass filtering may be used. As used herein, high pass filtering may refer to a method of passing signals with a frequency higher than a specific frequency and attenuating signals with a frequency lower than the specific frequency. The original phase image may be transformed into the k-space data by Fourier transform; a part of data in a central region of the k-space may be retained and the rest of the k-space data may be replaced by a constant, e.g., zero, thereby providing a filtered k-space. The size of the central region of the k-space where the k-space data are retained may be referred to as the kernel size. The filtered k-space may be transformed into a new image by inverse Fourier transform. The new image may include the low spatial frequency information and may be referred to as a low pass filtered image. The original phase image may be divided by the low pass filtered image so that the low spatial frequency information may be removed, and a high pass filtered image may be obtained. Merely by way of example, the kernel size may be 8×8 pixels, 16×16 pixels, 32×32 pixels, 64×64 pixels, or the like. In some embodiments, a two-dimensional (2D) high pass filtering or a three-dimensional (3D) high pass filtering may be performed.

In some embodiments, the processed phase image may be a phase image with the phase wrap-around artifact removed or reduced, a phase image with the background field removed or reduced, or a phase image with both the phase wrap-around artifact and the background field removed or reduced.

In some embodiments, if a plurality of original phase images are generated in step 610, each original phase image may be processed independently. For example, each original phase image may be processed to reduce or remove wrapped phase using an algorithm based on a single-echo sequence, respectively. In some embodiments, if a plurality of original phase images are generated in step 610, the original phase images may be processed together. For example, the original phase images may be processed to reduce or remove wrapped phase using an algorithm based on a multi-echo sequence.

In step 630, a virtual phase map may be generated based on the processed phase images (e.g., the processed phase images with the phase wrap-around artifacts removed or reduced). The generation of the virtual phase map may be performed by the virtual phase computing block 606. In some embodiments, a virtual phase at a pixel location corresponding to a virtual echo time may be computed. In some embodiments, the virtual phase may be computed by estimating the value of a variable (e.g., the virtual phase) on the basis of its relationship with another variable (e.g., the echo time, etc.). In some embodiments, the relationship may be obtained by fitting a continuity equation or a discrete equation. Theoretically, the more the data points (e.g., phase information corresponding to different echo times) are, the more accurate the fitting result may be. In some embodiments, the number of data points needed for fitting may be 2-20. In some embodiments, the fitting method may include interpolation, extrapolation, smoothing, regression analysis, the least square method, or the like, or any combination thereof. Exemplary interpolation methods may include Lagrange interpolation, Newton interpolation, Hermite interpolation, piecewise interpolation, spline interpolation, linear interpolation, or the like, or a combination thereof. Exemplary extrapolation methods may include linear extrapolation, polynomial extrapolation, conic extrapolation, French curve extrapolation, or the like, or a combination thereof. Exemplary regression analysis may include linear regression, nonlinear regression, multiple regression, logistic regression, partial regression, or the like, or a combination thereof. As an example, a linear equation may be fitted and used to compute the virtual phase at a pixel location corresponding to an echo time (see details in FIG. 8-A).

In step 640, a phase mask may be determined based on the virtual phase map or the processed phase image. The determination of the phase mask may be performed by the phase mask computing block 608. In some embodiments, the phase mask may be further used to generate a susceptibility weighted image. In some embodiments, different phase masks may be used under different conditions including, e.g., the characteristic of a tissue of interest (e.g., paramagnetism or diamagnetism), the characteristic of the acquisition system (e.g., the right-handed coordinate system or the left-handed coordinate system), or the like.

In some embodiments, the phase mask may be designed to suppress or enhance phases within certain ranges, and the contrast of the tissue of interest presented in the image may be enhanced. In some embodiments, the phase mask may vary in amplitude between 0 and 1. For example, in some embodiments, for a paramagnetic object in a right-handed coordinate system or for a diamagnetic object in a left-handed coordinate system, the variation of the phase over time may be negative. In this case, the phase mask may be designed in the following manner: if a pixel with a phase of which the value is less than zero (e.g., between $-\pi$ and 0), the phase mask may be designed to be between 0 and 1 to suppress the phase of which the value is less than zero at the pixel; if a pixel with a phase of which the value is larger than zero (e.g., between 0 and $\pi$), the phase mask may be designed to be equal 1, which may exert no effect on the phase of which the value is larger than zero at the pixel. This phase mask described above may be referred to as a negative phase mask. As another example, for a paramagnetic object in a left-handed coordinate system or for a diamagnetic object in a right-handed coordinate system, the variation of the phase over time may be positive. In this case, the phase mask may be designed in the following manner: if a pixel with a phase of which the value is larger than zero (e.g., between 0 and $\pi$), the phase mask may be designed to be between 0 and 1 to suppress the phase of which the value is larger than zero at the pixel; if a pixel with a phase of which the value is less than zero (e.g., between $-\pi$ and 0), the phase mask may be designed to be equal 1, which may exert no effect on the phase of which the value is less than zero at the pixel. Such a phase mask may be referred to as a positive phase mask.

In some embodiments, when the phase mask multiplies the original magnitude image or the magnitude map, if the value of the phase mask is 1, the phase mask may exert no effect on the original magnitude image or the magnitude map. If the value of the phase mask is less than 1, the phase mask may suppress the corresponding phase and enhance the contrast of the original magnitude image or the magnitude map.

It should be noted that the above description of the process for obtaining a phase mask is merely provided for the purposes of illustration, and not intended to limit the scope of the present disclosure. For persons having ordinary skills in the art, multiple variations or modifications may be made under the teachings of the present disclosure. For example, in some embodiments, step 630 may be unnecessary to the process for obtaining a phase mask. As another example, the processed phase image may be displayed and analyzed directly if desired. In some embodiments, the process of background field removal may be unnecessary. However, those variations and modifications do not depart from the scope of the present disclosure.

FIG. 7-A is a diagram of an exemplary gradient echo (GRE) sequence including monopolar readout gradients in a single repetition time (TR) according to some embodiments of the present disclosure. As used herein, the repetition time may refer to the time between the applications of two consecutive excitation RF pulses. The gradient echo (GRE) sequence shown in FIG. 7-A is suitable for application in the MRI system described elsewhere in the present disclosure. As illustrated, four echoes including an echo 711, an echo 712, an echo 713, and an echo 714 may be acquired from the gradient echo (GRE) sequence. The gradient echo (GRE) sequence 700 may include an excitation RF pulse 702. The excitation RF pulse 702 may be used to tip a portion of the longitudinal magnetization of a region of interest (ROI) into the transverse plane. θ° may refer to the flip angle of the excitation RF pulse 702. As used herein, the flip angle is the rotation of the net magnetization vector by a radio frequency pulse relative to the main magnetic field. In some embodiments, the flip angle of the excitation RF pulse 702 may be any value (e.g., 90°). Further, in some embodiments, the flip angle of the excitation RF pulse 702 may be less than 90°.

As shown in FIG. 7-A, 703 may represent the slice selection gradient. In some embodiments, the slice selection gradient 703 may be imposed along an axis perpendicular to the plane of the desired slice, resulting in a linear variation of potential resonance frequencies in that direction; a tailored RF pulse may be applied, of which the frequency components may match the range of frequencies contained in the desired slice. The slice selection gradient 703 and the RF pulse 702 may be combined such that the desired slice is excited. In some embodiments, the smaller downward projecting lobe in the slice selection gradient 703 immediately after the RF pulse 702 may be referred to as a slice-rephasing lobe. The slice-rephasing lobe may correct the phase dispersion of transverse magnetization that occurs concomitant with application of the main slice selection gradient. In some embodiments, for a 3D ME-GRE sequence, a phase encoding gradient 704 may be applied along the slice selection direction to spatially encode the echoes. In some embodiments, a spoiler 705 may be applied along the slice selection direction to destroy residual transverse magnetization.

As shown in FIG. 7-A, 706 may represent the phase encoding gradient along the phase encoding direction. The phase encoding gradient 706 may be used to spatially encode the echoes. For example, before the acquisition of the echo 711, the phase encoding gradient 706 may be applied. The phase encoding gradient 706 may be applied to adjust the echo signal. For example, the phase encoding gradient 706 may be applied when the acquisition of echo 711 is completed to eliminate the effects caused by the phase encoding gradient 706.

As shown in FIG. 7-A, 708 may represent the readout gradient. The readout gradient 708 may be used to spatially encode the echoes. For example, during the acquisition of the echo 711, the readout gradient 708 may be applied. In some embodiments, for a 3D ME-GRE sequence, with the phase encoding gradient 704, the phase encoding gradient 706 and the readout gradient 708, the echo 711 may be spatially encoded. A spatially encoded echo may correspond to a k-space trajectory and may be used to perform k-space sampling and construct MR images subsequently. According to the encoding gradients in FIG. 7-A, a Cartesian trajectory may be generated. In some embodiments, other Cartesian trajectories and non-Cartesian trajectories may be generated by adjusting the encoding gradients. Non-Cartesian trajectory may include, for example, radial, spiral, zigzag, propeller, or the like, or any combination thereof. In some embodiments, the method of filling the k-space may vary by adjusting the encoding gradients. For example, the k-space may be under-sampled, over-sampled, or fully sampled. The data may be filled into the k-space in any order, such as from the center outward, from left to right, from the top down.

In some embodiments, the readout gradient 708 may be used to generate echo signals. In some embodiments, a gradient echo (GRE) may be produced by a single RF pulse in conjunction with a gradient reversal. For example, following the RF pulse 702, a negative-going lobe of the readout gradient 707 may be applied, which may cause a phase dispersion of the precessing spins. When the readout gradient is reversed, for example, a positive-going lobe of the readout gradient 708 is applied, the spins may refocus and form a gradient echo 711. If a single-echo is generated in a repetition time (TR), the gradient echo (GRE) sequence may be referred to as the single gradient echo (GRE) sequence. In some embodiments, the same gradient reversal process used to create a single gradient echo may be repeated to produce two or more additional gradient echoes after a single RF pulse, and it may be referred to as the multi-echo gradient echo sequence. For example, as shown in FIG. 7-A, the second half of the upward gradient lobe of the readout gradient 708 may dephase the signal. The first half of the downward lobe of the readout gradient 709 may rephrase the spins and generate a second echo 712. The echo 713 and the echo 714 may be generated in the similar way. In some embodiments, the center of an echo may correspond to the center of a corresponding readout gradient. In some embodiments, the center of an echo may correspond to any position of a corresponding readout gradient. In some embodiments, a rewinder or a spoiler 710 may be applied along the readout direction to adjust the echo signal(s).

In some embodiments, in the multi-echo gradient echo sequence, an echo may correspond to an echo time (TE). As used herein, the echo time (TE) may refer to the time from the center of the first RF pulse (e.g., the excitation RF pulse) to the center of the echo in a single repetition time. As shown in FIG. 7-A, within a single repetition time, the echo time of the echo 711 may be shortest, while the echo time of the echo 714 may be longest. In some embodiments, the echo signals generated from a multi-echo gradient echo sequence may be equidistant or non-equidistant. In some embodiments, because of T2 relaxation, the signal intensity of each echo may be different. As shown in FIG. 7-A, within a TR, the signal intensity of the echo 711 may be the strongest, and while the signal intensity of the echo 714 may be the weakest.

In some embodiments, the gradient echo sequence 700 may be a two-dimensional (2D) gradient echo sequence or a three-dimensional (3D) gradient echo sequence. As show in FIG. 7-A, the gradient echo sequence 700 may be an ME-GRE sequence. In some embodiments, the gradient echo sequence 700 may be a GRE-EPI (echo planar imaging) sequence other than an ME-GRE sequence. In some embodiments, according to the method of filling the k-space, the GRE-EPI sequence may include the original sequence, the blipped echo planar single technique (BEST) sequence, the spiral sequence, or the like.

In some embodiments, in order to reduce or avoid the artifacts caused by the flow (or motion) of the tissue of interest (e.g., blood), a flow compensation may be performed along the slice selection direction, the phase encoding gradient, the readout gradient, etc. In some embodiments, the effect of flow compensation may be realized by an additional gradient lobe. In some embodiments, the effect of flow compensation may be realized by adjusting the parameters of the encoding gradients (e.g., the intensity, the length, the starting time, etc.). In some embodiments, the effect of flow compensation may be realized by the combination of the additional gradient lobe and the adjustment of the encoding gradients. In some embodiments, in the multi-echo gradient sequence, flow compensation may be performed on one or more echoes corresponding to specific echo times.

FIG. 7-B is a diagram of an exemplary gradient echo (GRE) sequence including bipolar readout gradients in a single repetition time (TR) according to some embodiments of the present disclosure. Similar to FIG. 7-A, the polarities of the readout gradients imposed on two adjacent echoes (e.g., the gradient 708 and the gradient 709) may be opposite. In this case, the readout gradients may be referred to as bipolar readout gradients (see details in FIG. 4-B). In some embodiments, for a multi-echo gradient sequence, the readout gradient may be bipolar or monopolar. As shown in FIG. 7-B, if the polarities of the readout gradients imposed on two adjacent echoes (e.g., the gradient 715 and the gradient 717) are the same, the readout gradients may be referred to as monopolar readout gradients. In this case, a fly back gradient (e.g., the gradient 716) may be inserted between any two adjacent readout gradients.

It should be noted that the above description of the gradient echo sequence is merely provided for the purposes of illustration, and not intended to limit the scope of the present disclosure. For persons having ordinary skills in the art, multiple variations or modifications may be made under the teachings of the present disclosure. For example, in some embodiments, the gradient echo (GRE) sequence 700 may further include a refocusing RF pulse after the excitation RF pulse 702 to generate a gradient and spin echo. However, those variations and modifications do not depart from the scope of the present disclosure.

FIG. 8-A is a flowchart illustrating a process for generating a susceptibility weighted image according to some embodiments of the present disclosure. In step 802, echo signals may be acquired. The echo signals may be acquired from a multi-echo gradient echo sequence. In some embodiments, the echo signals acquired from the multi-echo gradient echo sequence may be equidistant or non-equidistant. In some embodiments, the gradient echo sequence may be a two-dimensional (2D) gradient echo sequence or a three-dimensional (3D) gradient echo sequence. In some embodiments, only one echo signal may be acquired from a single gradient echo sequence. In some embodiment, in order to reduce or avoid the artifacts caused by the flow (or motion) of the tissue of interest (e.g., blood), a flow compensation may be performed along the slice selection encoding direction, the phase encoding gradient, or the readout gradient. In some embodiments, the phase information and the magnitude information may be obtained from the echo signals.

In step 804, the system may determine whether to process the phase information. If the answer is "yes," that is, the phase information is to be processed, the process may proceed to step 806 to generate an original phase image. If the answer is "no," that is, no phase information is to be processed, the process may proceed to step 820 to generate an original magnitude image.

In step 806, one or more original phase images may be generated. In some embodiments, an original phase image may correspond to an echo signal. For example, if a single-echo signal is acquired, only one set of original magnitude images corresponding to the same echo time may be generated. As another example, multiple sets of original phase images may be generated based on a plurality of echo signals corresponding to different echo times. The method of generating the original phase image may include single channel imaging, or multi-channel imaging.

Exemplary multi-channel imaging algorithms may include Weighted Average Method (as described in Hammond et al., Neuroimage, 39: 1682-1692 (2008), which is hereby incorporated by reference), Adaptive Coil Combine (ACC), the method of performing zero-order phase correction to the other channels relative to a reference channel and then performing multi-channel combination, or the like, or any combination thereof.

In step 808, the original phase image may be processed. In some embodiments, the original phase image may reflect the spatial distribution of the field incorrectly because of the effect of interference factors (e.g., phase wrap-around artifact, background field, noise, or the like). As an example, the original phase information at a pixel location corresponding to an echo time may be represented according to Equation (4) below:

$$\varphi(r,t) = \gamma B_{Local}(r)t + \gamma B_{BG}(r)t + \varphi_0(r) + \varepsilon(r,t),\qquad\text{Equation (4)}$$

where $\varphi(r,t)$ may represent the original phase information, r may represent the pixel location, t may represent the echo time, γ may represent the gyromagnetic ratio of the proton, $B_{Local}(r)$ may represent the local field distribution, $B_{BG}(r)$ may represent the background field distribution, $\varphi_0(r)$ may represent a constant phase offset, and $\varepsilon(r,t)$ may represent the noise-induced phase variation. In some embodiments, the local field distribution $B_{Local}(r)$ and the background field distribution may collectively referred to as "field distribution". For example, the field distribution may include a local field distribution, a background field distribution, or a combination of the local field distribution and the background field distribution.

In some embodiments, a process of phase unwrapping may be performed to remove the phase wrap artifacts caused by the limited phase storage range of (−π, π]. An unwrapped phase map may be generated based on the process of phase unwrapping. The phase unwrapping algorithms may include an algorithm based on a single-echo sequence (as described in, for example, Abdul-Rahman et al., Applied Optics, 46(26): 6623-6635 (2007)) and an algorithm based on a multi-echo sequence (as described in, for example, Feng et al., Magnetic Resonance in Medicine, 70(1): 117-126 (2013), which is hereby incorporated by reference). In some embodiments, the algorithm based on a single-echo sequence may include a global error-minimization method (e.g., the least-square algorithm, etc.), a residue-balancing method, a quality-guided algorithm, or the like.

In step 810, the system may determine whether to compute a virtual phase. If the answer is "yes," that is, a virtual phase is to be computed, the process may proceed to step 812 to select a virtual echo time. If the answer is "no," that is, no virtual phase is to be computed, the process may proceed to step 818 to determine a phase mask based on the processed phase image.

In step 812, a virtual echo time may be selected. The virtual echo time may be selected based on a default setting of the imaging system 100, or instructions from an operator (e.g., a doctor). As is known, in order to obtain a susceptibility weighted image with a good contrast, different tissues may correspond to different echo signals with different echo times. In some embodiments, the virtual echo time may be any positive number. In some embodiments, a plurality of virtual echo times may be selected. The number of the virtual echo times may be any positive number. In some embodiments, the virtual echo time may be selected according to the characteristic of the tissue of interest (e.g., susceptibility). See, for example, FIG. 8-B and the description thereof.

In step 814, a virtual phase may be computed based on the processed phase images and the selected virtual echo time. As described in FIG. 6-B, as an example, a linear equation may be fitted and used to compute the virtual phase. For example, theoretically, if the interference factors are omitted or left out, the relationship between the phase at a pixel location and the echo time may be expressed by Equation (5) below:

$$\varphi_p(r,t) = \gamma B_{Local}(r)t,\qquad\text{Equation (5)}$$

where $\varphi_p(r,t)$ may represent the virtual phase at a pixel location corresponding to an echo time without the effect of the interference factors (e.g., a phase wrap-around artifact and/or a background field, etc.). In some embodiments, the $B_{Local}(r)$ may be computed by fitting Equation (4) based on the phase information corresponding to different echo times. For example, a local field distribution map $B_{Local}(r)$ may be generated. As used herein, fitting, or referred to as curve fitting, refers to the process of constructing a curve, or a mathematical function, that has a best fit to a number of data points, possibly subject to one or more constraints. Theoretically, the more the data points (e.g., phase information corresponding to different echo times) are, the more accurate the fitting result may be. In some embodiments, the number of data points needed for fitting may be 2-20, which means that 2-20 echoes corresponding to different echo times or 2-20 processed phase images corresponding to different echo times may be needed for fitting. When the fitting equation is obtained, the slope of the fitting equation may be $B_{Local}(r)$. The method of obtaining the local field distribution $B_{Local}(r)$ may include linear regression, extrapolation, a graphing method, or the like, or any combination thereof. In some embodiments, the virtual phase may be computed by fitting a linear equation (e.g., Equation (5)) through linear interpolation based on local field distribution map $B_{Local}(r)$. In some embodiments, the number of the interpolation may be any positive number. For example, any virtual echo time corresponding to any positive number may be determined in the local field distribution map, and a corresponding virtual phase may be computed based on the virtual echo time and the local field distribution map according to a linear interpolation.

In step 816, a virtual phase map may be generated based on the virtual phase and the processed phase image. In some embodiments, a background field removal may be performed to the virtual phase map. Through the background field removal, the effect of $B_{BG}(r)$ may be reduced or removed. Exemplary method of reducing or removing background field may include SHARP (as described in, for example, Schweser et al., NeuroImage, 54(4): 2789-2807 (2011), which is hereby incorporated by reference).

In some embodiments, the process of phase unwrapping (e.g., in step 808) and the process of background field removal may be performed simultaneously. Exemplary algorithms used to remove or reduce the phase wrap-artifacts and the background field simultaneously may include Projection onto Dipole Field, high pass filtering, or the like, or any combination thereof. Merely by way of example, the background field may be removed or reduced using Equation (6) below:

$$\varphi'_1(r,t) = \gamma B_{Local}(r)t + \varepsilon'_1(r,t), \quad \text{Equation (6)}$$

where $\varphi'_1(r,t)$ may represent the processed phase information, $\varepsilon'_1(r,t)$ may represent a noise-induced phase variation. $\varepsilon'_1(r,t)$ may be different from $\varepsilon(r,t)$ because of the processing (e.g., phase unwrapping and/or background field removal) of the original phase information.

In some embodiments, the process of background field removal may be unnecessary. In some embodiments, if the background field is removed or reduced together with the phase wrap-around artifacts in step 808, the process may proceed to step 818 to determine a phase mask after the virtual phase map is generated.

In step 818, a phase mask may be determined based on the virtual phase map or the processed phase image. In some embodiments, the phase mask may be designed to suppress several certain phases at several pixel locations. As described in FIG. 6-B, different phase masks may be used under different conditions including, e.g., the characteristic of the tissue of interest (e.g., paramagnetism or diamagnetism), the characteristic of the coordinate system (e.g., the right-handed coordinate system or the left-handed coordinate system), or the like. For example, in some embodiments, for a paramagnetic object in a right-handed coordinate system or for a diamagnetic object in a left-handed coordinate system, the variation of the phase over time may be negative. In this case, the phase mask may be designed according to Equation (7) below:

$$g(r) = \begin{cases} (\varphi(r) + \pi)/\pi, & \varphi(r) < 0 \\ 1, & \varphi(r) > 0 \end{cases}, \quad \text{Equation (7)}$$

where r may represent the pixel location, g(r) may represent the phase mask, and $\varphi(r)$ may represent the corresponding phase at the pixel location. Merely by way of example, as to Equation (7), for pixels with a phase of $-\pi$, the phases of $-\pi$ at the pixels may be essentially completely suppressed, and for pixels with a phase whose value is between $-\pi$ and 0, the phases between $-\pi$ and 0 at the pixels may be only partly suppressed, for pixels with a phase whose value is between 0 and $\pi$, the phases at the pixels may be not affected by the phase mask. The phase mask expressed in Equation (7) may be a negative phase mask. As used herein, "essentially," as in "essentially completely," etc., with respect to a parameter or a characteristic may indicate that the variation is within 2%, or 5%, or 8%, or 10%, or 15%, or 20% of the parameter or the characteristic, or an average value of the parameter in, for example, a scintillation crystal array or a scintillation crystal module, etc.

In some embodiments, for a paramagnetic object in a left-handed coordinate system or for a diamagnetic object in a right-handed coordinate system, the variation of the phase over time may be positive. In this case, the phase mask may be designed according to Equation (8) below:

$$g(r) = \begin{cases} (\pi - \varphi(r))/\pi, & \varphi(r) > 0 \\ 1, & \varphi(r) < 0 \end{cases}, \quad \text{Equation (8)}$$

where r may represent the pixel location or pixel for brevity, g(r) may represent the phase mask, and $\varphi(r)$ may represent the phase at the pixel location r. As another example, as to Equation (8), for pixels with a phase of $\pi$, the phases of $\pi$ at the pixels may be essentially completely suppressed, for pixels with a phase whose value is between 0 and $\pi$, the phases between 0 and $\pi$ at the pixels may be only partly suppressed, for pixels with a phase whose value is between $-\pi$ and 0, the phases between $-\pi$ and 0 at the pixels may be not affected by the phase mask. The phase mask in Equation (8) may be a positive phase mask. After the phase mask is determined, at least some steps starting from node B as illustrated in FIG. 8-B may be performed.

In step 820, one or more original magnitude images may be generated. In some embodiments, an original magnitude image may correspond to an echo signal. For example, if a single-echo signal is acquired, only one set of original magnitude images corresponding to the same echo time may be generated. As another example, multiple sets of original magnitude images may be generated based on a plurality of echo signals corresponding to different echo times. The method of generating an original magnitude image may include single-channel imaging, or multi-channel imaging. Exemplary multi-channel imaging algorithms may include Sum of Square (SOS), Adaptive Coil Combine (ACC), or the like, or any combination thereof. If the k-space is under-sampled, exemplary multi-channel imaging algorithm may include SENSE, SMASH, GRAPPA, or the like, or a combination thereof.

In step 822, a T2* magnitude map (and/or a R2* magnitude map) may be generated based on the original magnitude images. As described in connection with FIG. 5, as an example, an exponential equation may be fitted and used to compute the T2* magnitude map. Theoretically, the more the data points (e.g., magnitude information corresponding to different echo times) are, the more accurate the fitting result may be. In some embodiments, the number of data points needed for fitting may be 2-20, which means 2-20 echoes corresponding to different echo times or 2-20 original magnitude images corresponding to different echo times may be needed for fitting. The exponential equation may be repressed as below:

$$S(TE) = S_0 \cdot e^{-TE/T2^*}, \quad \text{Equation (9)}$$

where S(TE) may represent the magnitude intensity at a pixel location corresponding to an echo time, $S_0$ may represent the magnitude intensity when TE=0. In some embodiments, a regression may be performed and T2* values corresponding to each echo time may be obtained. Exemplary methods may include extrapolation, a graphing method, or the like, or any combination thereof. In some embodiments, an R2* magnitude map may be generated based on the T2* magnitude map. The relationship between R2* and T2* may be expressed as below;

$$R2^* = 1/T2^*. \quad \text{Equation (10)}$$

In step 824, the system may determine whether to compute a T2* mask. If the answer is "yes," that is, a T2* mask is to be computed, the process may proceed to step 826 to determine a T2* mask based on the T2* magnitude map. If the answer is "no," that is, no T2* mask is to be computed, the process may proceed to step 828.

In step 826, a T2* mask may be determined based on the T2* magnitude map (or the R2* magnitude map). In some embodiments, the T2* mask may be expressed as below:

$$h(r) = 1 - (T2^*(r) - \text{thresh})/\text{scale}, \quad \text{Equation (11)}$$

where r may represent the pixel location, h(r) may represent the T2* mask, thresh may represent a threshold, scale may represent a normalization factor. In some embodiments, thresh and scale may be obtained based on the distribution of the T2* values of the T2* magnitude map, empirical equations, a default setting of the imaging system 100, or instructions from an operator (e.g., a doctor). After the T2* mask is determined, at least some steps starting from node C as illustrated in FIG. 8-B may be performed.

In step 828, a virtual echo time may be selected (see details in FIG. 8-B). In step 830, a virtual magnitude may be computed based on the original magnitude images and the selected virtual echo time. As described in connection with FIG. 5, as an example, an exponential equation may be fitted and used to compute the virtual magnitude at a pixel location corresponding to an echo time. For example, the relationship between the magnitude and echo time may be expressed as Equation (9). As another example, the virtual magnitude may be computed by fitting an exponential equation (e.g., Equation (9)) through linear interpolation based on the original magnitude image corresponding to different echo times. In some embodiments, the virtual time selected in step 828 may be the same or different with that selected in step 812.

In step 832, a virtual magnitude map may be generated based on the original magnitude image and the virtual magnitude. In some embodiments, after the original magnitude images are generated in step 820, the process may proceed to step 834 to generate an average magnitude map. In some embodiments, the original magnitude information may be combined and averaged to obtain the average magnitude map. For example, the method of computing the average magnitude map may be expressed as below:

$$M = (P_1(t_1)f_1 + P_2(t_1)f_2 P_3(t_3)f_3 + \ldots + P_k(t_k)f_k)/k, \quad \text{Equation (12)}$$

where M may represent the average magnitude map, $t_1, t_2, t_3, \ldots, t_k$ may represent different echo times, $P_1, P_2, P_3, \ldots, P_k$ may represent the magnitude images corresponding to different echo times, $f_1, f_2, f_3, \ldots, f_k$ may represent weights for each magnitude image. In some embodiments, the weights $f_1, f_2, f_3, \ldots, f_k$ may be determined based on empirical values, default setting of the imaging system 100, instructions from an operator (e.g., a doctor), or the like. After the virtual magnitude map or the average magnitude map is generated, at least some steps starting from node A as illustrated in FIG. 8-C may be performed.

It should be noted that the above description of the process for generating a susceptibility weighted image is merely provided for the purposes of illustration, and not intended to limit the scope of the present disclosure. For persons having ordinary skills in the art, multiple variations or modifications may be made under the teachings of the present disclosure. For example, in some embodiments, if the T2* mask is not computed and the virtual magnitude map is computed by using linear interpolation, step 822 may be unnecessary in the process for generating a susceptibility weighted image described in FIG. 8-A. However, those variations and modifications do not depart from the scope of the present disclosure.

FIG. 8-B is a flowchart illustrating a process for selecting a virtual echo time according to some embodiments of the present disclosure. In step 850, a tissue type may be identified in the region of interest. In some embodiments, the tissue type may be a kind of tissue, or a plurality of tissues that may be with similar characteristic (e.g., susceptibility). In some embodiments, the tissues may include bone, tooth, intracranial calcification, basal ganglia, hemorrhagic spot, or the like, or a combination thereof.

In step 860, a virtual echo time may be selected based on the susceptibility of the tissue type. In the region of interest of an object, different tissues in the image may present different contrasts according to different echo times. For example, for some small tissues (e.g., the small vein) or tissues with weak susceptibility (e.g., basal ganglia), a long echo time (e.g., TE=20 milliseconds at 3T) may be selected and the contrast of the tissue presented in the susceptibility weighted image may be enhanced. For some tissues with strong susceptibility (e.g., hemorrhagic spot), because of inhomogeneity of the field around the tissue, a phase wraparound artifact may occur, therefore a short echo time (e.g., TE=10 milliseconds as 3T) may be suitable. In some embodiments, based on the susceptibility of the tissue type, a plurality of virtual echo times may be selected. The number of the virtual echo times may be any positive number. For a specific tissue type, to obtain a desired image contrast, an optimal number of virtual echo times may be determined. Different tissues types may be correspond to different optimal numbers of virtual echo times.

FIG. 8-C is a flowchart illustrating a process for generating a susceptibility weighted image according to some embodiments of the present disclosure. In some embodiments, the method of generating a susceptibility weighted image may be expressed as below:

$$S(r)_{SWI} = Q^n(r)S(r), \quad \text{Equation (13)}$$

where $S(r)_{SWI}$ may represent the susceptibility weighted image, Q(r) may represent a mask, S(r) may represent a magnitude image or a magnitude map. The mask herein may be the phase mask, the T2* mask, or the weighted mask generated based on the phase mask and the T2* mask. The mask may be applied by any number of times n (n is an integer) to the magnitude image or the magnitude map to obtain a susceptibility weighted image with different contrasts. In some embodiments, the larger the value of n is, the higher the contrast of the tissue of interest may be, however, the lower the signal to noise ratio (SNR) may be. Merely by way of example, n may be set as 3 or 4.

As illustrated, in step 836, the phase mask may multiply the virtual magnitude map or the average magnitude map. In step 838, the T2*mask may multiply the virtual magnitude map or the average magnitude map. In step 840, the phase mask may be combined with the T2* mask, and a weighted mask may be generated. Then the weighted mask may multiply the virtual magnitude map or the average magnitude map. In step 842, a susceptibility weighted image may be generated based on the mask and the magnitude image or the magnitude map.

In some embodiments, the susceptibility weighted image may be processed to obtain a new composite image that may be with a better contrast and image quality. In some embodiments, a minimum intensity projection (MinIP) may be performed on the susceptibility weighted image. As used herein, a minimum intensity projection may be a data visualization method that enables detection of low-density structures in a given volume. When a set of rays pass through an image, pixels with low-density may be retained and projected onto a plane to generate a minimum intensity projection image. The minimum intensity projection may be used to assess how well a tissue of interest is represented in an image or otherwise visualized. According to the method of minimum intensity projection, an image may be searched along a set of rays in a given direction and the smallest value along the rays may be selected and included in a projection image at a same position. In some embodiments, the minimum intensity projection may be applied to the original magnitude image, the magnitude map, the original phase image, or the processed phase image.

It should be noted that the above description of the process for generating a susceptibility weighted image is merely provided for the purposes of illustration, and not intended to limit the scope of the present disclosure. For persons having ordinary skills in the art, multiple variations or modifications may be made under the teachings of the present disclosure. For example, in some embodiments, the phase mask, the T2* mask, or the weighted mask generated based on the phase mask and the T2* mask may multiply the original magnitude image to generate a susceptibility weighted image. However, those variations and modifications do not depart from the scope of the present disclosure.

EXAMPLES

The examples are provided for illustrated purposes and not intended to limit the scope of the present disclosure.

Example 1

FIG. 9-A through FIG. 9-C illustrate three exemplary images produced by the signals acquired from the brain with different image producing procedures according to some embodiments of the present disclosure. As illustrated in FIG. 9-A, an original phase image was generated based on the original phase information according to a multi-channel imaging. Then the phase information regarding the scalp was removed, and the next steps regarding phase calculation or phase processing were performed on the phase information regarding the brain only. As illustrated in FIG. 9-B, a phase unwrapping was performed using a phase unwrapping method and the phase wrap around artifacts were removed. As illustrated in FIG. 9-C, the background field was removed using a background field effect removal method. After the phase was unwrapped and the background field was removed, the residual phase information may be further processed, e.g., a phase mask may be generated based on the residual phase information.

Example 2

FIG. 10-A through FIG. 10-E illustrate five exemplary images produced by the signals acquired from the brain with different image producing procedures according to some embodiments of the present disclosure. As illustrated in FIG. 10-A, an original phase image was generated based on the original phase information according to a multi-channel imaging. A high-pass filtering (the kernel size of the high pass filter was 32×32) was performed, and there were residual phase wrap around artifacts above the nasal cavity (as illustrated in FIG. 10-B). As illustrated in FIG. 10-C, a susceptibility weighted image was generated based on phase image illustrated in FIG. 10-B. As illustrated in FIG. 10-D, a phase unwrapping was performed using a phase unwrapping method, and the background field was removed using a background field effect removal method. Before the phase unwrapping and background field effect removal, the phase information regarding the scalp was pre-removed. As illustrated in FIG. 10-E, then a susceptibility weighted image was generated based on the phase image with phase unwrapped and background field removed illustrated in FIG. 10-D. It may be seen from FIG. 10-E that no residual phase wrap around artifacts occurred.

Example 3

FIG. 11-A through FIG. 11-C illustrate three exemplary images or maps produced by the signals acquired from the brain with different image producing procedures according to some embodiments of the present disclosure. As illustrated in FIG. 11-A, an original magnitude image was generated based on the magnitude information according to a multi-channel imaging. As illustrated in FIG. 11-B, a T2* magnitude map was generated based on T2* related information taken into calculation. As illustrated in FIG. 11-C, an average magnitude map was calculated based on the magnitude information of the signals. The original magnitude image, the T2* magnitude map and/or the average magnitude map may be further used to generate a susceptibility weighted image.

Example 4

FIG. 12-A through 12-C illustrate three exemplary minimum intensity projections produced by the signals acquired from the brain with different image producing procedures according to some embodiments of the present disclosure. As illustrated in FIG. 12-A, a short echo time was set, and a susceptibility weighted image was generated based on the echo signal(s) with a short echo time. A minimum intensity projection corresponding to the susceptibility weighted image was generated. Similarly in FIG. 12-B and FIG. 12-C, two minimum intensity projections corresponding to the susceptibility weighted images were generated based on the echo signals with a middle echo time and a long echo time respectively. It may be seen from the images that different echo times may correspond to different image contrasts.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities of ingredients, properties such as molecular weight, reaction conditions, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method for magnetic resonance imaging implemented on at least one device each of which has at least one processor and storage, the method comprising:
   acquiring a plurality of echo signals relating to a region of interest of a subject at a number of echo times, each echo signal corresponding to an echo time;
   generating a plurality of phase images based on the plurality of echo signals, each phase image corresponding to an echo signal;
   generating an unwrapped phase map by performing a phase unwrapping correction to the plurality of phase images;
   generating a virtual phase map based on the unwrapped phase map, the virtual phase map comprising at least a virtual phase corresponding to a virtual echo time;
   determining a phase mask based on the virtual phase map;
   obtaining magnitude information of the plurality of echo signals; and
   generating a susceptibility weighted image based on the phase mask and the magnitude information.

2. The method of claim 1, wherein the virtual echo time is a positive number.

3. The method of claim 1, the acquiring the plurality of echo signals comprising:
   performing a flow compensation along a readout direction and/or a phase encoding direction.

4. The method of claim 1, the virtual echo time relating to a feature of a tissue in the region of interest.

5. The method of claim 4, the feature of the tissue type comprising the susceptibility of the tissue type.

6. The method of claim 1, the generating a virtual phase map comprising:
   obtaining a field distribution map according to phase information of the plurality of phase images;
   determining, based on the field distribution map, a virtual echo time; and
   determining, based on the virtual echo time and the field distribution map, a virtual phase.

7. The method of claim 6, the determining a virtual phase comprising:
   determining the virtual phase using a method selected from linear interpolation, the least square method, or linear regression.

8. The method of claim 1, the generating a virtual phase map comprising:
   eliminating a background field from the plurality of phase images; or
   eliminating a background field from the virtual phase map.

9. The method of claim 1, the determining a phase mask comprising:
   applying a normalization to the virtual phase map.

10. The method of claim 1, the magnitude information comprising an original magnitude image, a virtual magnitude map, an average magnitude map, a T2* magnitude map, or a T2* mask.

11. The method of claim 10, wherein the virtual magnitude map is generated based on the T2* magnitude map.

12. The method of claim 10, the virtual magnitude map comprising a virtual magnitude determined based on the original magnitude image.

13. The method of claim 12, wherein the virtual magnitude is determined using a method selected from linear interpolation, the least square method, or linear regression.

14. The method of claim 10, the generating a susceptibility weighted image comprising:
   computing a weighted result of the phase mask and the T2* mask; and
   obtaining the susceptibility weighted image by multiplying the weighted result by at least one of the original magnitude image, the virtual magnitude map, or the average magnitude map.

15. The method of claim 10, the generating a susceptibility weighted image comprising:
   multiplying the phase mask by at least one of the original magnitude image, the virtual magnitude map, or the average magnitude map.

16. The method of claim 1, further comprising:
   performing a minimum intensity projection on the susceptibility weighted image.

17. A system, comprising:
   at least one storage medium including a set of instructions for magnetic resonance imaging;
   at least one processor in communication with the at least one storage medium, wherein when the at least one processor executes the set of instructions, the system is caused to:
   acquire a plurality of echo signals relating to a region of interest of a subject at a number of echo times, each echo signal corresponding to an echo time;
   generate a plurality of phase images based on the plurality of echo signals, each phase image relating to an echo signal;
   generate an unwrapped phase map by performing a phase unwrapping correction to the plurality of phase images;
   generate a virtual phase map based on the unwrapped phase map, the virtual phase map comprising at least a virtual phase corresponding to a virtual echo time;
   determine a phase mask based on the virtual phase map;
   obtain magnitude information of the plurality of echo signals; and
   generate a susceptibility weighted image based on the phase mask and the magnitude information.

18. The system of claim 17, wherein the system is further caused to:
   obtain a field distribution map according to phase information of the plurality of phase images;
   determine, based on the field distribution map, a virtual echo time; and
   determine, based on the virtual echo time and the field distribution map, a virtual phase.

19. The system of claim 17, wherein the virtual echo time is a positive number.

20. The system of claim 17, the magnitude information comprising an original magnitude image, a virtual magnitude map, an average magnitude map, a T2* magnitude map, or a T2* mask.

* * * * *